US010449105B2

(12) United States Patent
Hollander

(10) Patent No.: US 10,449,105 B2
(45) Date of Patent: Oct. 22, 2019

(54) SYSTEM AND METHOD OF BIDIRECTIONAL COMPLIANT JOINT TORQUE ACTUATION

(71) Applicant: SpringActive, Inc., Tempe, AZ (US)

(72) Inventor: Kevin Hollander, Scottsdale, AZ (US)

(73) Assignee: SpringActive, Inc., Tempe, AZ (US)

( * ) Notice: Subject to any disclaimer, the term of this patent is extended or adjusted under 35 U.S.C. 154(b) by 1031 days.

(21) Appl. No.: 14/923,072

(22) Filed: Oct. 26, 2015

(65) Prior Publication Data

US 2016/0113831 A1  Apr. 28, 2016

Related U.S. Application Data

(60) Provisional application No. 62/068,726, filed on Oct. 26, 2014, provisional application No. 62/086,976, filed on Dec. 3, 2014.

(51) Int. Cl.
A61H 3/00 (2006.01)
A61F 2/68 (2006.01)
A61F 5/01 (2006.01)
A61H 1/02 (2006.01)

(52) U.S. Cl.
CPC .............. A61H 3/00 (2013.01); A61F 2/68 (2013.01); A61F 5/0102 (2013.01); A61H 1/0244 (2013.01); A61H 1/0266 (2013.01); A61F 2005/0155 (2013.01); A61F 2005/0197 (2013.01); A61H 2003/007 (2013.01); A61H 2201/0192 (2013.01); A61H 2201/123 (2013.01); A61H 2201/1207 (2013.01); A61H 2201/1215 (2013.01); A61H 2201/1238 (2013.01); A61H 2201/149 (2013.01); A61H 2201/164 (2013.01); A61H 2201/165 (2013.01);
(Continued)

(58) Field of Classification Search
CPC .... A61H 3/00; A61H 2003/007; A61H 3/008; A61H 1/0237; A61H 1/024; A61H 1/0244; A61H 1/0262; A61F 2/68; A61F 2002/741; A61F 2/64
See application file for complete search history.

(56) References Cited

U.S. PATENT DOCUMENTS 7,578,799 B2 *  8/2009  Thorsteinsson ...... A61B 5/1038
                                                     602/16
7,628,766 B1 * 12/2009  Kazerooni ............. A61F 5/00
                                                     602/16
(Continued)

Primary Examiner — Alvin J Stewart
(74) Attorney, Agent, or Firm — Robert D. Atkins; Patent Law Group Atkins and Associates, P.C.

(57) ABSTRACT

A joint actuation device for adding torque to a joint of a user includes an actuation system having an actuator and a spring. A lever is configured to couple to the user's leg and to the actuation system. The lever configured to rotate at a device joint with respect to the actuation system. A first sensor measures a position of the device joint. A second sensor measures deflection in a spring. The actuator is positioned based on the position of the device joint and deflection in the spring. The actuator is configured to deflect the spring to apply a torque the device joint. The device joint aligns with the user's joint to add a torque to the user's joint during a gait activity. The actuator disengages the spring during a non-gait activity. The lever is configured to disengage from the actuator when the device joint exceeds a predetermined angle.

22 Claims, 23 Drawing Sheets

(52) U.S. Cl.
CPC ............... *A61H 2201/1628* (2013.01); *A61H 2201/5097* (2013.01)

(56) References Cited

U.S. PATENT DOCUMENTS

| | | | |
|---|---|---|---|
| 7,985,193 B2* | 7/2011 | Thorsteinsson | A61B 5/1038 602/16 |
| 8,702,632 B2* | 4/2014 | Han | A61F 5/0102 601/23 |
| 8,968,223 B2* | 3/2015 | Ikeuchi | A61H 3/008 601/23 |
| 9,044,346 B2* | 6/2015 | Langlois | A61F 2/60 |
| 9,662,262 B2* | 5/2017 | Hollander | B25J 9/0006 |
| 9,682,005 B2* | 6/2017 | Herr | A61H 3/00 |
| 9,682,006 B2* | 6/2017 | Goldfarb | A61H 3/00 |
| 9,687,377 B2* | 6/2017 | Han | A61F 5/0125 |
| 9,687,409 B2* | 6/2017 | Teng | A61H 1/024 |
| 9,889,058 B2* | 2/2018 | Horst | A61H 1/024 |
| 9,907,722 B2* | 3/2018 | Aguirre-Ollinger | A61H 3/00 |
| 10,016,332 B2* | 7/2018 | Aguirre-Ollinger | A61H 3/00 |
| 10,278,885 B1* | 5/2019 | Smith | A61H 3/008 |
| 2004/0064195 A1* | 4/2004 | Herr | A61F 2/66 623/24 |
| 2007/0054777 A1* | 3/2007 | Kawai | A61H 3/00 482/1 |
| 2007/0056592 A1* | 3/2007 | Angold | A61H 3/00 128/845 |
| 2007/0106190 A1* | 5/2007 | Katoh | A61F 5/0102 602/26 |
| 2007/0267791 A1* | 11/2007 | Hollander | F16F 1/125 267/177 |
| 2008/0039756 A1* | 2/2008 | Thorsteinsson | A61B 5/1038 602/23 |
| 2008/0097269 A1* | 4/2008 | Weinberg | A61F 2/68 602/16 |
| 2008/0188907 A1* | 8/2008 | Aguirre-Ollinger | A61H 1/0237 607/48 |
| 2009/0131839 A1* | 5/2009 | Yasuhara | A61F 5/0102 601/5 |
| 2009/0227424 A1* | 9/2009 | Hirata | A61B 5/1038 482/7 |
| 2009/0270766 A1* | 10/2009 | Yasuhara | A61H 3/00 600/595 |
| 2009/0299243 A1* | 12/2009 | Hirata | A61F 5/0193 602/23 |
| 2010/0049102 A1* | 2/2010 | Yasuhara | A61H 1/0244 601/5 |
| 2010/0094188 A1* | 4/2010 | Goffer | A61H 3/008 602/23 |
| 2010/0113988 A1* | 5/2010 | Matsuoka | A61H 3/008 601/34 |
| 2010/0234777 A1* | 9/2010 | Yasuhara | B25J 9/0006 601/35 |
| 2010/0298746 A1* | 11/2010 | Shimizu | A61H 3/008 601/35 |
| 2011/0264016 A1* | 10/2011 | Han | A61F 5/0102 601/35 |
| 2012/0157894 A1* | 6/2012 | Hiki | A61H 1/024 601/35 |
| 2012/0259431 A1* | 10/2012 | Han | A61F 5/0125 623/24 |
| 2013/0012852 A1* | 1/2013 | Imaida | A61F 5/01 602/16 |
| 2013/0197408 A1* | 8/2013 | Goldfarb | A61F 5/0102 601/35 |
| 2013/0261766 A1* | 10/2013 | Langlois | A61F 2/60 623/33 |
| 2013/0296746 A1* | 11/2013 | Herr | A61H 3/00 601/34 |
| 2014/0100493 A1* | 4/2014 | Craig | A61H 3/00 601/35 |
| 2014/0142475 A1* | 5/2014 | Goldfarb | A61H 3/00 601/35 |
| 2014/0196757 A1* | 7/2014 | Goffer | A61H 3/02 135/66 |
| 2014/0200491 A1* | 7/2014 | Julin | A61H 3/00 601/35 |
| 2014/0276265 A1* | 9/2014 | Caires | A61H 3/00 601/34 |
| 2014/0330431 A1* | 11/2014 | Hollander | B25J 9/0006 700/245 |
| 2014/0378882 A1* | 12/2014 | Kazerooni | A61F 5/01 602/19 |
| 2015/0025423 A1* | 1/2015 | Caires | A61H 1/024 601/35 |
| 2015/0142130 A1* | 5/2015 | Goldfarb | A61H 1/024 623/25 |
| 2015/0150694 A1* | 6/2015 | Pusch | A61F 2/60 623/24 |
| 2015/0173929 A1* | 6/2015 | Kazerooni | A61F 5/0125 602/16 |
| 2015/0209214 A1* | 7/2015 | Herr | A61H 3/00 623/27 |
| 2015/0230964 A1* | 8/2015 | Kazerooni | A61F 5/02 602/16 |
| 2015/0231018 A1* | 8/2015 | Shim | A61H 3/00 623/24 |
| 2015/0272809 A1* | 10/2015 | Accoto | A61H 1/0237 623/31 |
| 2015/0272810 A1* | 10/2015 | Teng | A61H 1/024 601/34 |
| 2015/0313786 A1* | 11/2015 | Sano | A61H 3/00 602/16 |
| 2015/0321341 A1* | 11/2015 | Smith | A61H 1/0237 623/27 |
| 2015/0351995 A1* | 12/2015 | Zoss | A61H 1/024 623/32 |
| 2015/0374573 A1* | 12/2015 | Horst | A61H 3/00 602/16 |
| 2016/0016309 A1* | 1/2016 | Swift | B25J 9/0075 623/24 |
| 2016/0023350 A1* | 1/2016 | Holgate | A45F 3/00 248/550 |
| 2016/0030271 A1* | 2/2016 | Roh | A61H 1/0277 602/16 |
| 2016/0030272 A1* | 2/2016 | Angold | A61H 1/024 623/24 |
| 2016/0038371 A1* | 2/2016 | Sandler | A61H 3/00 602/19 |
| 2016/0045385 A1* | 2/2016 | Aguirre-Ollinger | A61H 3/00 623/24 |
| 2016/0139666 A1* | 5/2016 | Rubin | B25J 11/003 345/633 |
| 2016/0229065 A1* | 8/2016 | Angold | A61H 1/0244 |
| 2016/0250093 A1* | 9/2016 | Koren | A61F 2/60 623/30 |
| 2016/0250094 A1* | 9/2016 | Amundson | A61H 1/024 623/24 |
| 2016/0262969 A1* | 9/2016 | Ohta | A61H 1/0255 |
| 2016/0310731 A1* | 10/2016 | Dixon | A61F 5/0127 |
| 2016/0331624 A1* | 11/2016 | Sankai | A61H 1/024 |
| 2016/0331625 A1* | 11/2016 | Sankai | B25J 9/0006 |
| 2017/0049659 A1* | 2/2017 | Farris | B25J 9/104 |
| 2017/0143573 A1* | 5/2017 | Boulanger | A61H 1/0237 |
| 2017/0246492 A1* | 8/2017 | Herr | A61H 3/00 |
| 2017/0340504 A1* | 11/2017 | Sanz Merodio | A61H 1/02 |
| 2017/0360645 A1* | 12/2017 | Sodeyama | A61H 3/00 |
| 2018/0066740 A1* | 3/2018 | Lee | A61F 2/68 |
| 2018/0092792 A1* | 4/2018 | Ohta | A61H 1/0244 |
| 2018/0098907 A1* | 4/2018 | Aguirre-Ollinger | A61H 3/00 |
| 2018/0110671 A1* | 4/2018 | Adams | A61H 3/02 |
| 2018/0160946 A1* | 6/2018 | Macko | A61B 5/4595 |
| 2018/0161188 A1* | 6/2018 | Zistatsis | A61H 1/02 |
| 2018/0177667 A1* | 6/2018 | Uemura | A61H 3/00 |
| 2018/0177668 A1* | 6/2018 | Park | A61H 1/024 |
| 2018/0177669 A1* | 6/2018 | Cho | A61H 3/00 |
| 2018/0177670 A1* | 6/2018 | Shim | A61H 3/00 |
| 2018/0177671 A1* | 6/2018 | Kim | A61H 3/00 |

(56) References Cited

U.S. PATENT DOCUMENTS

| | | | |
|---|---|---|---|
| 2018/0177672 A1* | 6/2018 | Uchida | A63B 21/4011 |
| 2018/0257216 A1* | 9/2018 | Shavit | A61H 1/0255 |
| 2018/0271690 A1* | 9/2018 | Edelstein | A61H 3/00 |
| 2018/0272524 A1* | 9/2018 | Ohtsubo | A61H 1/024 |
| 2018/0272525 A1* | 9/2018 | Kumeno | B25J 9/0006 |
| 2018/0338883 A1* | 11/2018 | Chavarria | A61H 3/00 |
| 2018/0369057 A1* | 12/2018 | John | A61H 3/00 |
| 2019/0015284 A1* | 1/2019 | Horst | A61H 3/00 |
| 2019/0015286 A1* | 1/2019 | Glaister | A61H 3/00 |
| 2019/0015287 A1* | 1/2019 | Witte | A61H 3/00 |

* cited by examiner

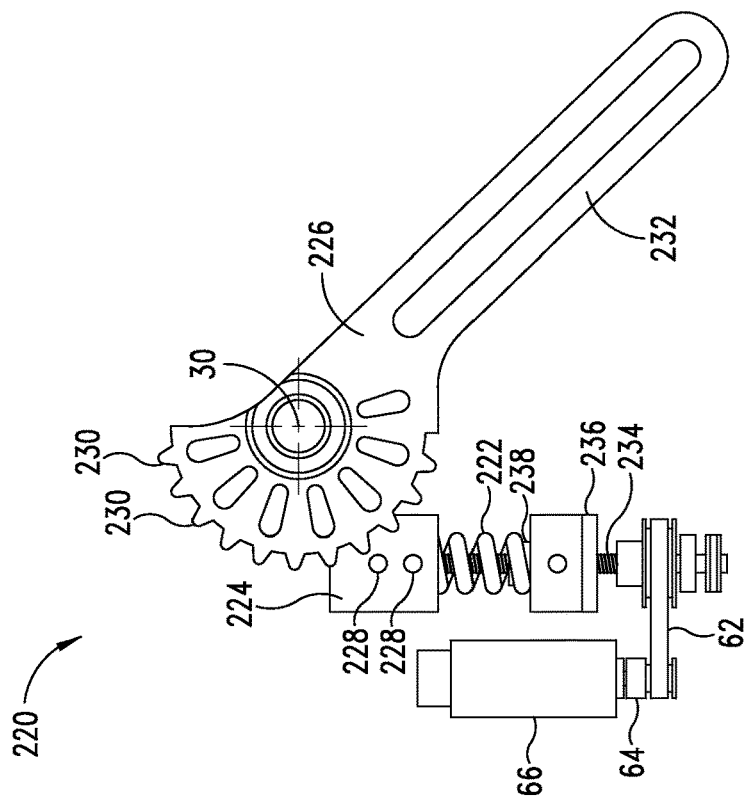
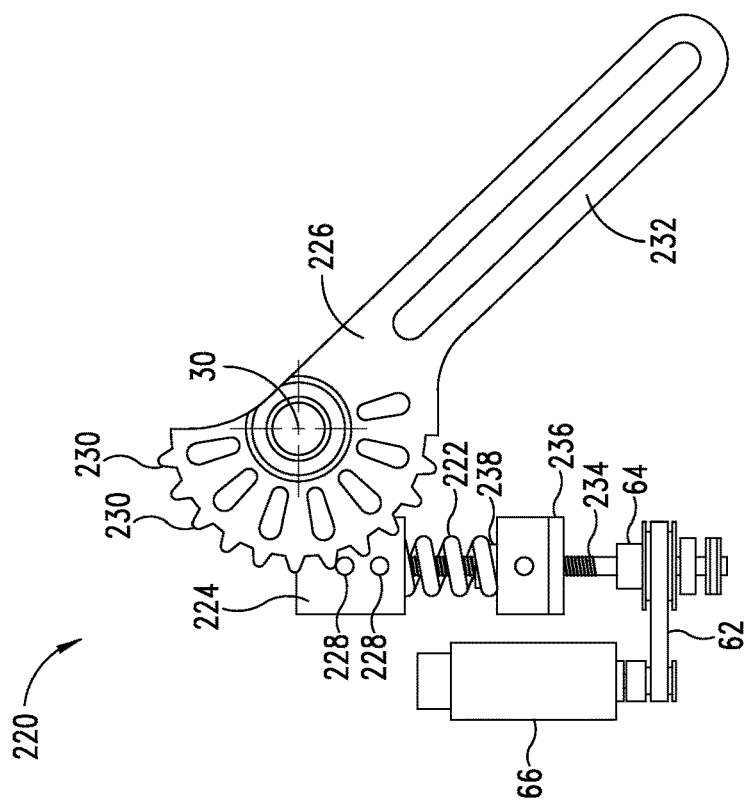

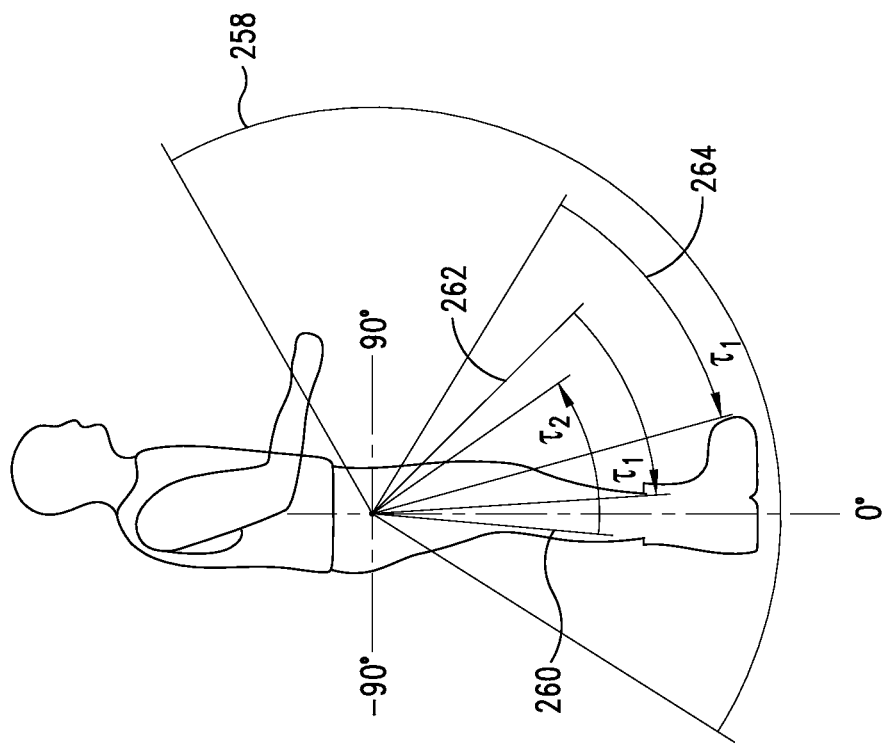
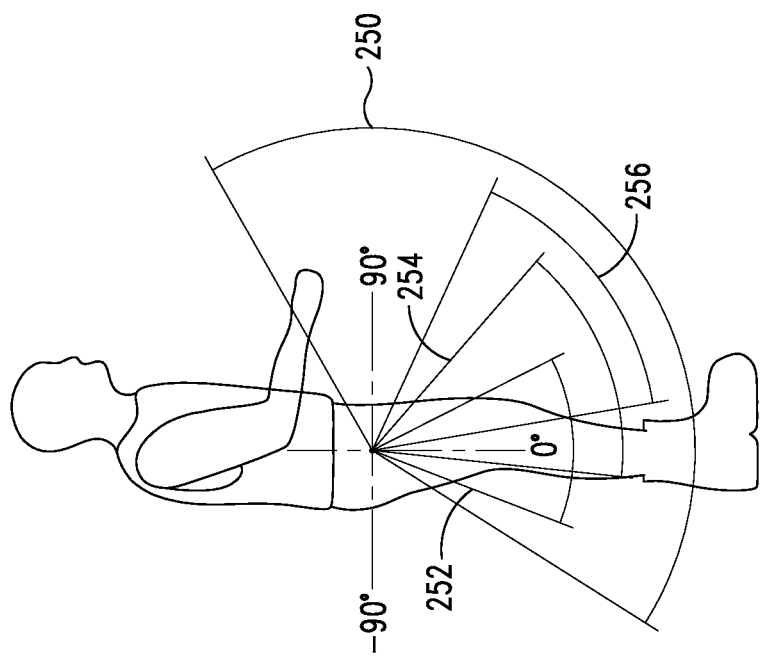
FIG. 12b
FIG. 12a

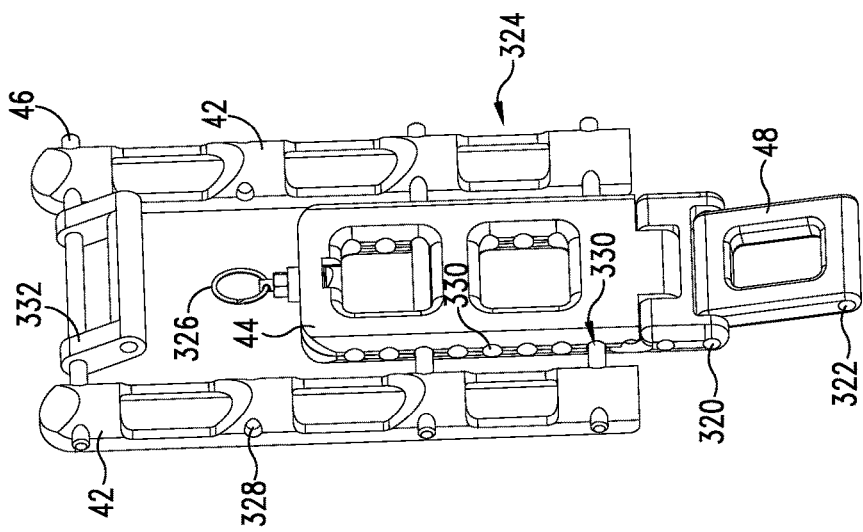
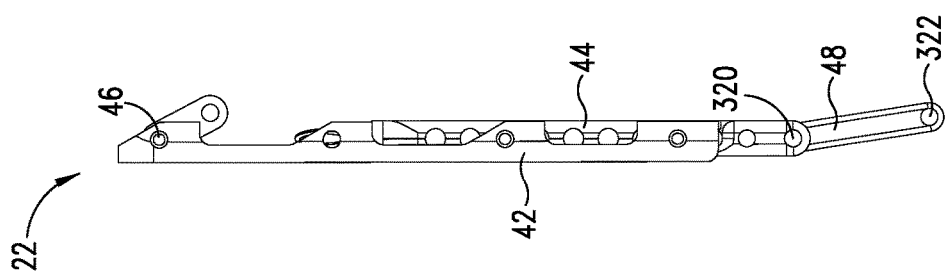
FIG. 18b
FIG. 18a

SYSTEM AND METHOD OF BIDIRECTIONAL COMPLIANT JOINT TORQUE ACTUATION

CLAIM TO DOMESTIC PRIORITY

The present application claims the benefit of U.S. Provisional Application No. 62/068,726, filed Oct. 26, 2014, and U.S. Provisional Application No. 62/086,976, filed Dec. 3, 2014, which applications are incorporated herein by reference.

FIELD OF THE INVENTION

The present invention relates in general to gait assistance systems and, more particularly, to bidirectional compliant joint torque augmentation systems.

BACKGROUND OF THE INVENTION

Human locomotion, such as walking and running, is commonly described in terms of gait or a gait cycle. Gait is a cyclical or reoccurring pattern of leg and foot movement, rotations, and torques that creates locomotion. Due to the repetitive nature of gait, gait is typically analyzed in terms of percentages of a gait cycle. A gait cycle is defined for a single leg beginning with the initial contact of the foot with a surface such as the ground. The initial contact of the foot on the ground is referred to as a heel strike. The conclusion of a gait cycle occurs when the same foot makes a second heel strike. A gait cycle can be divided into two phases: stance phase and swing phase. Stance phase describes the part of the gait cycle where the foot is in contact with the ground. Stance phase begins with heel strike and ends when the toe of the same foot leaves the ground. Swing phase describes the part of the gait cycle where the foot is in the air and not in contact with the ground. Swing phase begins when the foot leaves contact with the ground and ends with the heel strike of the same foot. For walking gait speed, stance phase typically describes approximately the first 50%-60% of the gait cycle, while swing phase describes approximately the remaining 40%-50% of the gait cycle.

Individuals have unique gait patterns. Energy or metabolic expenditure during an individual's gait depends on several factors including, body mass, stride length, step rate, and other physical and environmental factors. Individuals have physical and metabolic limits, which determine the speed and distance an individual can travel on foot. Injury or disease may affect a person's range of motion or gait efficiency. Carrying heavy loads may also reduce gait efficiency. Carrying significant loads over long distances and time periods can lead to fatigue and cause musculoskeletal injuries. Military personnel are considered particularly at risk for fatigue and injury from carrying loads. As the quantity and complexity of gear used in military duty has increased, the weight of loads carried by military personnel has also increased. Many soldiers carry a variety of devices, such as night goggles, global positioning systems (GPS), body armor, and other gear. Although maximum loads are recommended, the recommended maximums are typically exceeded. Typical loads carried by soldiers can range between 45 kilograms (kg) to 60 kg or more. Soldiers often carry the loads for long distances while marching on foot.

The relationship between distance traveled and the rate of metabolic energy expended is exponential in nature. The metabolic cost of gait depends on the speed of gait, the physical ability of the individual, and the weight of a load carried by the individual. When carrying a heavier load, the speed of a march is decreased in order to avoid fatigue. Fatigue has been shown to have detrimental effects on individuals who carry the heavy loads. Fatigue is known to increase likelihood of acute injury by raising the potential for trips and falls. Fatigue can also affect mental focus, reduce situational awareness, and negatively impact overall physical and mental performance. Non-combat related injuries caused by carrying significant loads are also a problem. Long term and chronic overuse injuries account for a significant amount of injuries for soldiers.

Individuals who lack able-bodied motion or gait may have a reduced range of motion at one or more joints or may be unable to supply the power to move a limb or a joint in an able-bodied path. Orthotic devices help restore mobility to people who lack able-bodied motion or gait. People who require a lower limb orthosis often expend more metabolic power to walk or move at the same speed as able-bodied individuals. One goal of lower limb orthotic devices is to help the user achieve a normal gait while reducing energy expended by the user.

Various types of structures and exoskeletons have been proposed to support gait. The human hip is a three degree-of-freedom joint that possesses a large range of motion. In addition to the kinematic flexibility of the human hip joint, the waist and hip size among individuals varies. Current exoskeletons are limited in ability to adjust to different size individuals or with different gait patterns. One example of current joint augmentation system for the hip supports only uni-directional motion. Other joint assistance structures interfere with the range of motion of the human joint, resulting in limited usefulness in combat conditions. Weight of wearable exoskeletons and wearable orthotics is also a concern. Joint assistance systems that are too heavy diminish or negate any joint assistance provided by the system.

SUMMARY OF THE INVENTION

A need exists for a compact wearable system that adds torque to the human joint in multiple directions while permitting a greater range of motion. Accordingly, in one embodiment, the present invention is a method of adding torque to a joint of a user comprising the steps of providing an actuation system including an actuator and a first and second spring, coupling a lever to a leg of the user and to the actuation system, measuring a position of the joint using a first sensor, and positioning the actuator to compress the first or second spring based on the position of the joint.

In another embodiment, the present invention is a method of adding torque to a joint of a user comprising the steps of coupling a lever to a leg of the user, and providing an actuator including a spring. The actuator is coupled to the lever. The method further includes the steps of measuring a position of the joint using a first sensor, and positioning the actuator to deflect the spring based on the position of the joint.

In another embodiment, the present invention is a joint actuation device comprising an actuation system including an actuator and a spring. A lever is coupled to the actuation system and is configured to couple to a leg of a user. The lever is configured to rotate at a device joint with respect to the actuation system. A first sensor is configured to measure a physical characteristic of the leg. A control system is configured to control the actuator based on the physical characteristic of the leg.

In another embodiment, the present invention is a joint actuation device comprising an actuation system including an actuator and a spring. A lever is coupled to the actuation system and is configured to couple to a leg of a user. The lever is configured to rotate at a device joint with respect to the actuation system.

BRIEF DESCRIPTION OF THE DRAWINGS

FIGS. 11a-11b illustrate an alternative compliant actuation assembly for a joint actuation system with enhanced range of motion;

FIGS. 12a-12b illustrate a schematic representation of the enhanced range of motion for a compliant joint actuation system;

FIGS. 18a-18c illustrate a torso attachment assembly for a compliant joint actuation system;

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, those skilled in the art will appreciate that the description is intended to cover alternatives, modifications, and equivalents as may be included within the spirit and scope of the invention as defined by the appended claims and their equivalents as supported by the following disclosure and drawings.

Exoskeletons for assisting human gait are disclosed herein for adding force or torque at the hip joints and ankle joints. The gait assisting exoskeletons reduce the user's metabolic expenditure during gait, thereby improving the user's gait efficiency and allowing the user to walk and carry heavy loads for greater time periods and over longer distances.

Figure 1:
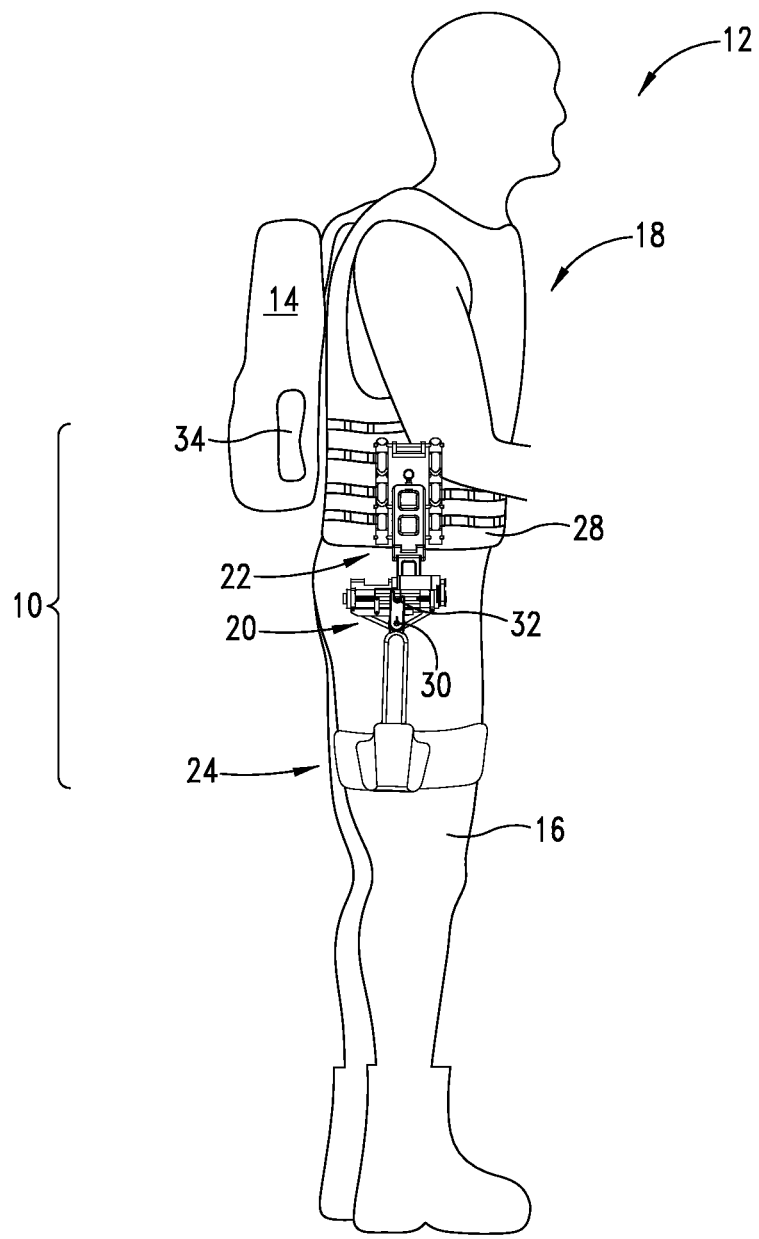
FIG. 1 illustrates a compliant joint actuation system worn at a hip joint of a user.

FIG. 1 shows a bi-directional compliant joint actuation system 10 worn by a user 12. A wearable device is disclosed for assisting a user with the movements associated with human gait by augmenting torque at the hip joint in each direction of hip motion, flexion and extension. As a user moves through a gait cycle, ground reaction forces act on the user's hip, knee, and ankle joints, and the user adds opposing torques to resist the forces. A user may carry a pack or a load 14, for example, worn as a backpack by user 12. A carried load increases the ground reaction forces on user 12, and user 12 expends more energy to counteract the forces. Carrying a pack or load 14 increases the metabolic requirements for user 12 to move, increases the user's rate of fatigue, and reduces the distance user 12 is able to travel by foot. User 12 wears a compliant joint actuation system 10 in order to add assistive energy to the user's step and reduce the metabolic cost of gait.

A bi-directional compliant joint actuation system 10 supplements the joint torques created by the user by supplying assistive torque to the human's joints at specific points throughout gait. For example, a bi-directional compliant joint actuation system 10 for the hip supplies a torque in a direction of hip extension during stance phase, and supplies a torque in the direction of hip flexion during swing phase. Adding force or torque at specific timing during the user's gait reduces metabolic energy required from user 12 to produce a gait step.

Compliant joint actuation system 10 is worn on each of the user's legs 16 and on each side of the user's torso 18, with the device spanning each hip joint in order to supply a force in the direction of motion of the user's legs 16 by adding a torque at the hip joint. In one embodiment, compliant joint actuation system 10 applies a force or torque at or near each hip joint of user 12 during both stance and swing phase of each gait step for each leg 16. A force or torque is supplied by the system in alternating directions during stance and swing phase. Applying torque in a first direction to leg 16 during swing phase assists user 12 with hip flexion. Applying torque in a second direction to leg 16 during stance phase assists user 12 with hip extension and the lifting of the body that occurs during early stance. With compliant joint actuation system 10, user 12 expends less energy to move at a normal gait.

Compliant joint actuation system 10 is configured to support a walking gait speed, and also may support other gait activities, including running, traversing a sloped surface, maneuvering up and down stairs, or traversing an uneven surface or terrain. Compliant joint actuation system 10 is configured to ensure non-gait activities are not encumbered by the system. Compliant joint actuation system 10 allows the user to sit, stand, squat, kneel, or move leg 16 in the coronal plane, sagittal plane, or transverse plane without resistance from the device. In one embodiment, where compliant joint actuation system 10 is designed specifically to add torque during a walking gait speed, compliant joint actuation system 10 is also designed to ensure user 12 can run and climb stairs without interference from the device. In another embodiment, compliant joint actuation system 10 is configured to support a range of gait speeds, including walking and running, and is configured to support a wide range of motion, including stair climbing. Where compliant joint actuation system 10 supports a range of motion by providing torque throughout that range of motion, the system also permits a greater range of motion beyond the torque-supported range of motion. Therefore, compliant joint actuation system 10 is designed to support gait activities, while allowing unencumbered motion beyond gait activities.

Compliant joint actuation system 10 includes a compliant actuation assembly 20, a torso attachment assembly 22, and a leg attachment assembly 24 for each side of user 12. A compliant joint actuation system 10 is worn on each leg 16 of user 12. Therefore, user 12 wears one or more compliant joint actuation systems 10 to assist with gait. A compliant joint actuation system 10 on each leg 16 provides bi-directional force or torque to each leg 16. Compliant joint actuation system 10 is configured to allow mobility and a natural range or motion for user 12 without encumbering or restricting the user's gait.

Torso attachment assembly 22 and leg attachment assembly 24 provide for wearability of compliant joint actuation system 10. The torques or forces from compliant actuation assembly 20 are transferred through attachment assemblies 22 and 24 to the limbs and joints of user 12. In one embodiment, user 12 wears leg attachment assembly 24 on upper legs or thighs and wears torso attachment assembly 22 on a belt or vest. For example, torso attachment assembly 22 is configured to interface with an improved outer tactical vest (IOTV) 28. Compliant joint actuation system 10 is secured to user 12 at two anatomical attachment points, such as torso 18 and leg 16, with the hip joint located between the two attachment points. Torso attachment assembly 22 and leg attachment assembly 24 are adjustable in order to fit compliant joint actuation system 10 onto different users and to align the system 10 with the user's joint.

Compliant actuation assembly 20 is disposed between torso attachment assembly 22 and leg attachment assembly 24. Compliant actuation assembly 20 includes a system joint 30, which operates as an effective hip joint. System joint 30 operates as the output of compliant joint actuation system 10. Compliant actuation assembly 20 is applied at system joint 30, and leg attachment assembly 24 rotates about system joint 30 with respect to compliant actuation assembly 20 and torso attachment assembly 22. Compliant actuation assembly 20 is disposed in proximity to the user's anatomical hip joint to align a system joint 30 of compliant joint actuation system 10 with the user's hip joint. Aligning effective hip joint 30 of the system with the user's anatomical hip joint results in efficient transfer of torque to the user's hip joint. A lever 32 is coupled to leg attachment assembly 24 and to compliant actuation assembly 20. Lever 32 rotates about system joint 30 to transfer the force or torque supplied by compliant actuation assembly 20 into the user's leg 16 through leg attachment assembly 24. By applying a force to lever 32, a torque is applied to leg 16 and ultimately adds an assistive torque at the user's anatomical hip joint.

Compliant joint actuation system 10 includes a control assembly or control system 34 configured to control compliant actuation assembly 20, which applies a force or torque to user 12 through torso attachment assembly 22 and leg attachment assembly 24. In one embodiment, control system 34 includes a microprocessor or microcontroller with one or more motor controllers, and a battery or other power source. For example, control system 34 includes one microprocessor and two motor controllers for controlling two compliant actuation assemblies 20, with one controller for each hip. Control system 34 is coupled wirelessly or by wired connection to compliant actuation assembly 20. Control system 34 can be mounted to user 12 remotely with respect to the location of control compliant actuation assembly 20. In one embodiment, control assembly 34 is carried in pack 14 or coupled externally to user 12. By coupling control system 34 to the torso 18 of user 12, rather than to legs 16, the weight of control assembly 34 is positioned for better gait dynamics than if control assembly were mounted to legs 16. Additional weight on the legs is avoided and compliant joint actuation system 10 performs better by further reducing metabolic cost and is more comfortable for user 12 to wear. Alternatively, control assembly 34 is mounted on a leg 16 of user 12 or at any point of attachment on user 12. In another embodiment, control system 34 is lightweight and is incorporated into the structure of compliant actuation assembly 20. In another embodiment, control assembly 34 is coupled to an exoskeleton, frame, or body armor, which is coupled to user 12 or worn by user 12.

Figure 2:
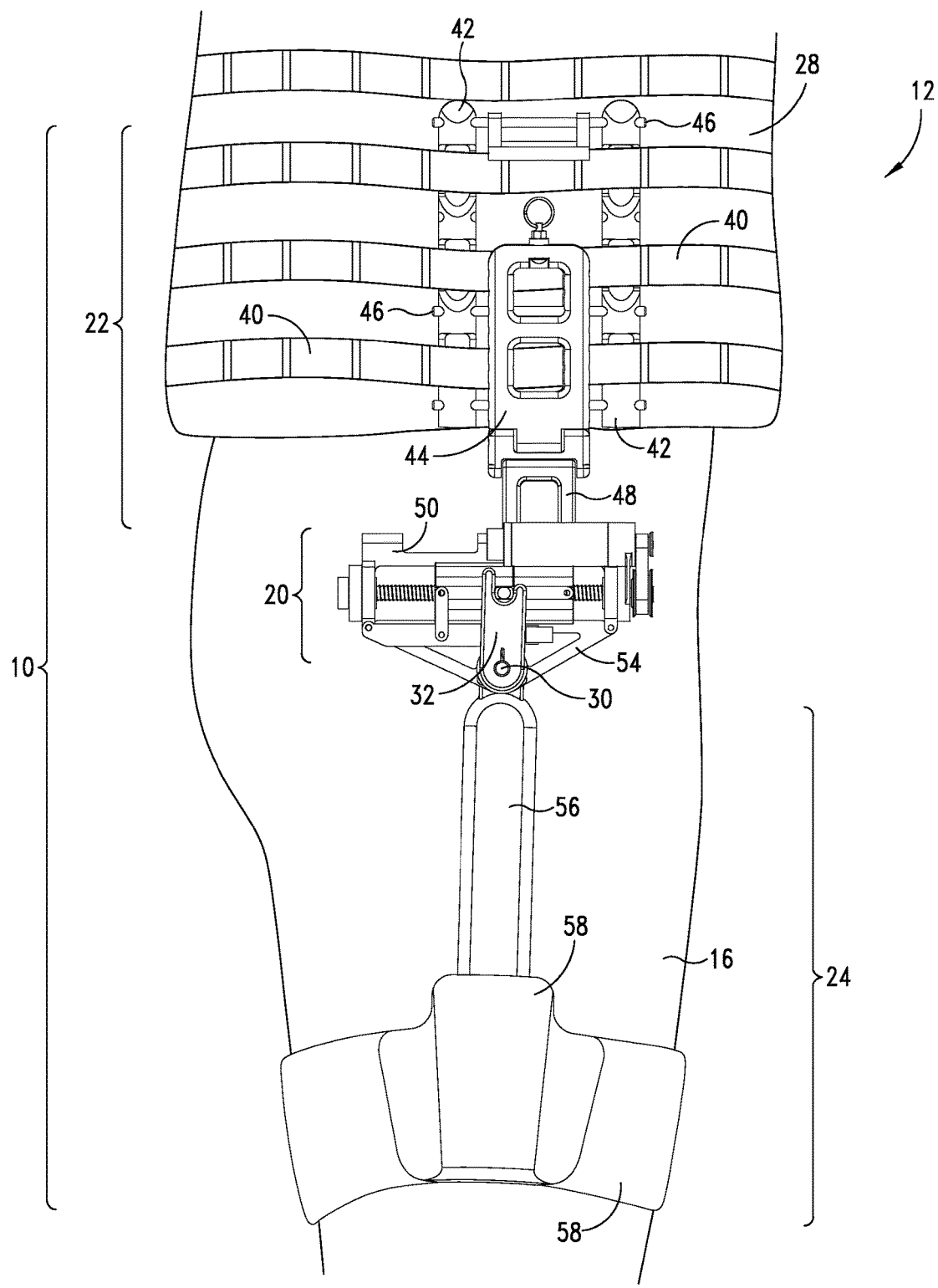
FIG. 2 illustrates a side view of a compliant joint actuation system worn at a hip joint of a user.

FIG. 2 shows additional detail of compliant joint actuation system 10 worn on the right side of user 12. User 12 also wears a compliant joint actuation system 10 on the left side (not shown). Compliant actuation assembly 20 operates to supply an output torque at system joint 30. In order to transfer an output torque at system joint 30 to the anatomical hip joint of user 12, compliant joint actuation system 10 comprises torso attachment assembly 22 and leg attachment assembly 24 to efficiently transfer the system's output torque to the user 12. Torso attachment assembly 22 holds components of compliant actuation assembly 20 in a fixed position with respect to the direction of torque applied. For example, torque is supplied at the hip in the sagittal plane, and torso attachment assembly 22 is configured to remain fixed on user 12 without rotating in the sagittal plane. Leg attachment assembly 24 holds lever 32 of compliant actuation assembly 20 in a fixed position on leg 16 with respect to the direction of torque applied. Lever 32 and leg attachment assembly 24 rotate together with respect to compliant actuation assembly 20 and torso attachment assembly 22 about system joint 30. Therefore, the output torque of compliant actuation assembly 20 is applied to the user's leg 16 though lever 32 and leg attachment assembly 24.

Torso attachment assembly 22 comprises a plurality of linkages that interface with a webbing 40 coupled to vest 28. In one embodiment, vest 28 with webbing 40 includes an IOTV with a ladder attachment system, such as a pocket attachment ladder system (PALS), having a matrix of 2.54 centimeter (cm) webbing. One or more stakes 42 fit within webbing 40, and are disposed between webbing 40 and vest 28. A locking rack 44 couples to stakes 42 by a plurality of pins 46. Pins 46 fit into both locking rack 44 and stakes 42 to hold locking rack 44 in place with respect to stakes 42. In one embodiment, stakes 42 fit vertically through a horizontal webbing, locking rack 44 is positioned between vertical stakes 42, and pins 46 extend horizontally through each stake 42 and through locking rack 44. Stakes 42 and pins 46 hold locking rack 44 in a vertical position to prevent rotation of locking rack 44 in the sagittal plane with respect to the torso 18.

Torso attachment assembly 22 couples to compliant actuation assembly 20 by a redundant link 48. Redundant link 48 may comprise one or more links and operates as a kinematically redundant link between torso attachment assembly 22 compliant actuation assembly 20. Redundant link 48 couples to locking rack 44 of torso attachment assembly 22 and to an upper bracket of compliant actuation assembly 20. In another embodiment, torso attachment assembly 22 includes a reinforced hip belt configured to couple to redundant link 48. Redundant link 48 allows upper bracket 50 to move medially or laterally and to rotate in the coronal plane with respect to locking rack 44. Redundant link 48 permits abduction and adduction of leg 16 and allows compliant joint actuation system 10 to fit a variety of body types.

Torso attachment assembly 22 is configured to efficiently transfer torques from compliant actuation assembly 20 to user 12. Materials of the components of torso attachment assembly 22 are selected to be rigid and lightweight and may include a metal, metal alloy, polymer, fiberglass, carbon fiber, composite material, natural material, or other suitable material. In one embodiment, torso attachment assembly 22 includes aluminum. As torque is generated by compliant actuation assembly 20, torso attachment assembly 22 reduces loss of energy from the system caused by unwanted rotation or bending of the components. User 12 is fitted with compliant joint actuation system 10 to align system joint 30 with the user's anatomical hip joint to further improve the efficiency of the system.

Compliant actuation assembly 20 couples to leg attachment assembly 24 through lever 32, which is rotationally mounted to a lower bracket 54 of compliant actuation assembly 20. Lower bracket 54 and upper bracket 50 operate as a rigid base to hold components of compliant actuation assembly 20. Lever 32 is rotationally or pivotally coupled to lower bracket 54 at system joint 30. An end of lever 32 opposite to compliant actuation assembly 20 is coupled to leg attachment assembly 24 at a thigh link 56. In one embodiment, thigh link 56 is flexible in the coronal plane to allow thigh link 56 to conform to the natural contour of leg 16, while being substantially rigid in the sagittal plane to reduce torque loss. Thigh link 56 attaches to leg 16 by a thigh panel 58, which couples to leg 16 of user 12. Thigh panel 58 is adjustable to fit different users. In one embodiment, thigh panel 58 includes a strap or support panel that provides a large surface area of material worn around the thigh. The forces from compliant joint actuation system 10 are applied to leg 16 through thigh link 56 and thigh panel 58. A surface area of thigh panel 58 is selected to distribute the torque or force from thigh link 56 to the user's leg 16 both efficiently and comfortably. Thigh panel 58 is large enough to distribute the forces of the system without interfering with the user's range of motion. In another embodiment, thigh panel 58 is incorporated into clothing or other wearable items. In yet another embodiment, compliant joint actuation system 10 is coupled to an exoskeleton, frame, or body armor, which is worn by user 12.

Figure 3A:
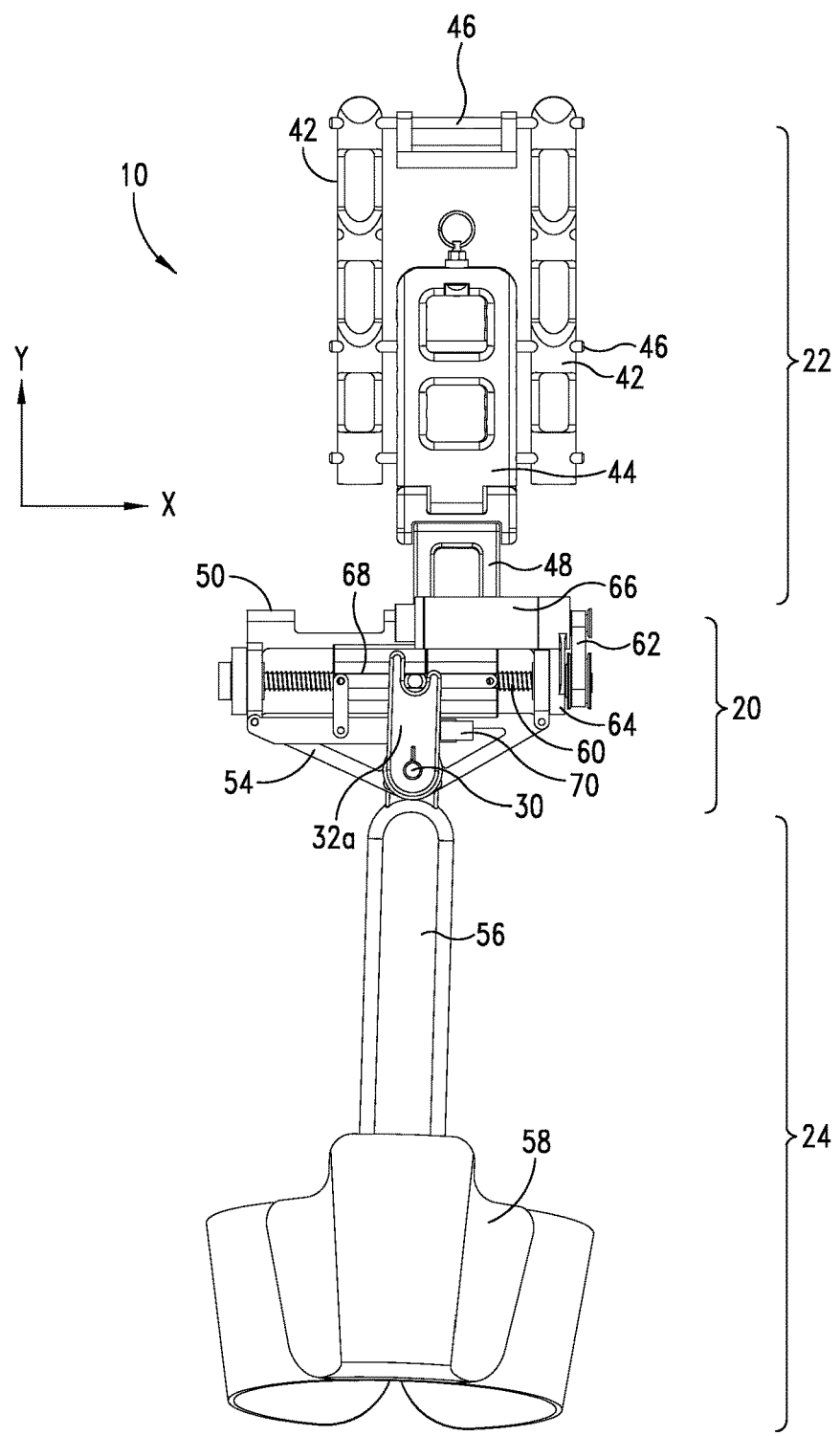
FIGS. 3a-3b illustrate a side view of a compliant joint actuation system in more detail.

FIG. 3a shows a lateral side of compliant joint actuation system 10 from FIG. 1 for the right hip. Compliant actuation assembly 20 includes an active compliant mechanism having one or more active elements and one or more compliant elements. Active elements may include motors or actuators. Compliant elements may include helical, coil, or torsional springs, leaf springs, cables having elastic properties, or other types of compliant device. In one embodiment, compliant actuation assembly 20 is powered by a plurality of compliant members, such as springs, and an active member, such as a motor-driven screw 60, arranged in series. In another embodiment, an active element of compliant actuation assembly 20 is powered by a controllable position actuator or a force-type actuator, and may include a hydraulic, pneumatic, rotary, direct-drive, series-elastic, electroactive polymer-based, chemical-based, or other actuation scheme.

A motor-driven screw 60 is driven by a belt drive assembly or belt 62 coupled by a bracket 64 to an actuator 66. Actuator 66 couples to screw 60 to rotate or drive screw 60 and produce rotary motion. Screw 60 includes bearings, such as radial bearings and thrust bearings, at each end of screw 60. Actuator 66 couples to one end of screw 60 to drive screw 60 in either the clockwise direction or counter-clockwise direction based on a command or motor control pattern received by actuator 66 from control system 34. Actuator 66 is a position-type actuator that positions a threaded nut, such as a lead screw, along screw 60. A support shell 68 contains the threaded nut, which is threaded onto screw 60 and which translates linearly along screw 60 as screw 60 is rotated by actuator 66. Actuator 66 is controlled by control system 34 from FIG. 1.

Compliant joint actuation system 10 is controlled using an input from one or more sensors 70. Sensors 70 may include one or more sensors disposed on compliant joint actuation system 10 or worn by user 12. Sensors 70 detect a physical characteristic or physical state of a mobile body, such as a limb of user 12 or a link of compliant joint actuation system 10. A sensor 70 may be disposed on a limb or joint of user 12, such as a hip joint, ankle joint, lower leg, thigh, foot, or other part of user 12 to measure or detect a physical characteristic of a limb or joint of user 12. Sensors 70 may be disposed on a joint, linkage, or other component of compliant joint actuation system 10 to measure or detect a physical characteristic of the system. For example, a sensor 70 coupled to support shell 68 by a nut sensor link 72 is used to measure a position of a nut within support shell 68. Sensors 70 may be disposed on the system to indirectly measure a physical characteristic of user 12. For example, a position sensor disposed on system joint 30 correlates to a position of the user's anatomical hip, and thus, the position measurement of a system joint provides information about a user's anatomical position.

A sensor 70 may include an accelerometer, vibrometer, rate gyro, potentiometer, inclinometer, pressure transducer, force transducer, load cell, or other sensor or combination of sensors. The physical characteristic or physical state measured by sensors 70 include a kinematic state, a loading state, or a kinematic state and a loading state. A kinematic state includes an angular position, linear position, linear velocity, angular velocity, linear acceleration, or angular acceleration associated with a mobile body with reference to a fixed global frame or a frame fixed to any other mobile body. A loading state includes a moment or force experienced by the mobile body. In one embodiment, sensors 70 continuously measure information about compliant joint actuation system 10 or about user 12.

Information from sensors 70 are used as inputs for control system 34, which produces an output command to actuator 66. In one embodiment, the output command is a position for actuator 66. The position of actuator 66 determines a force that is applied to lever 32 by compliant actuation assembly 20, and lever 32 operates as an end effector of the system. In one embodiment, lever 32 interfaces with both the medial and lateral sides of compliant actuation assembly 20. Lever 32 includes a medial or inner lever 32a, shown in FIG. 3a, and a lateral or outer lever 32b, shown in FIG. 3b.

Figure 3B:
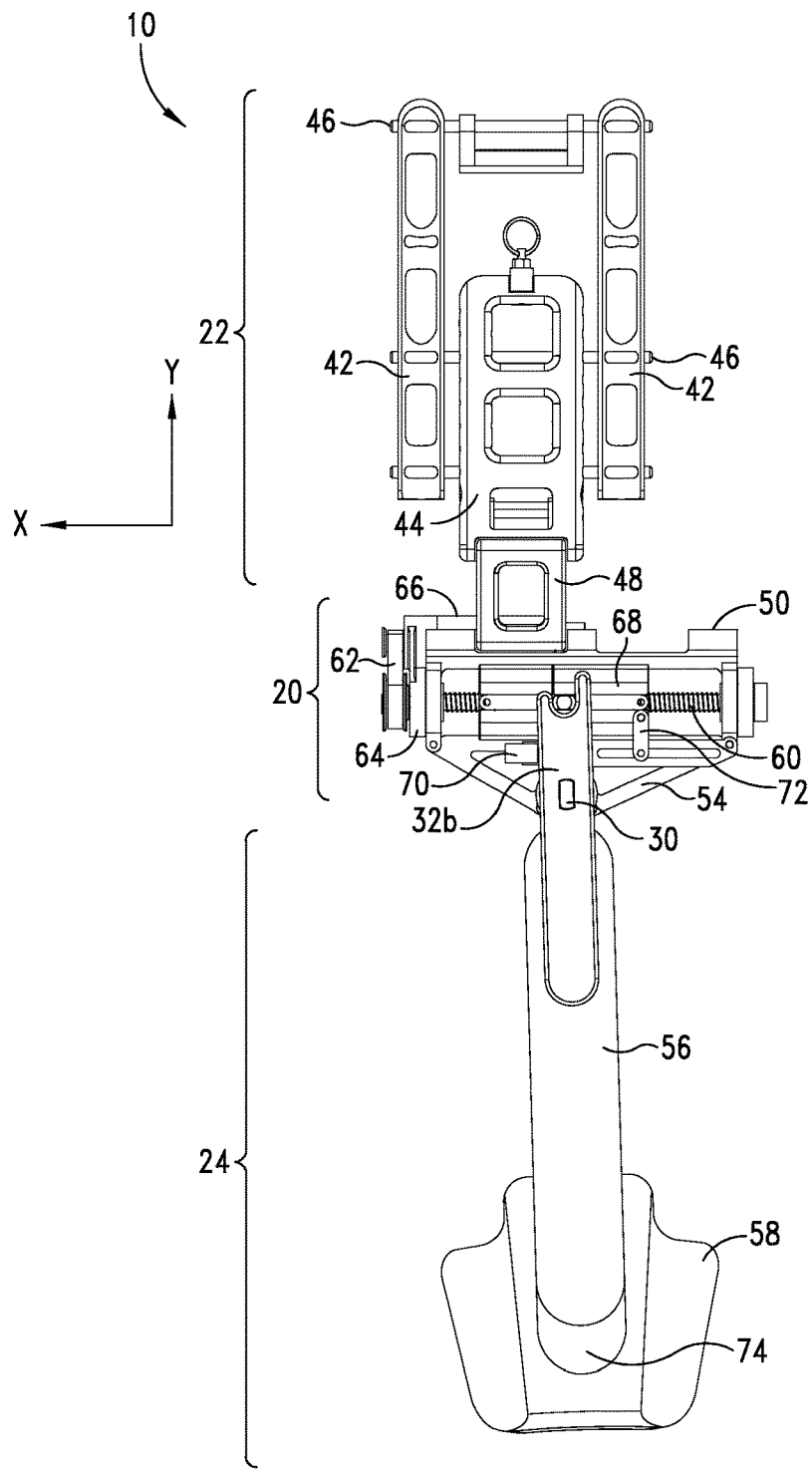

FIG. 3b shows a medial side of compliant joint actuation system 10 for the right hip. Inner lever 32b and outer lever 32a are rigidly coupled together or are comprised of a single piece. Inner lever 32b and outer lever 32a rotate together with respect to lower bracket 54 at system joint 30. Inner lever 32b extends distally from compliant actuation assembly 20 along the user's thigh and terminates at a thigh link 56. In one embodiment, inner lever 32b is rigidly attached to thigh link 56 by a fixed joint. In another embodiment, inner lever 32b is coupled to thigh link 56 by a prismatic joint or slip joint that permits translation of inner lever 32b along the y-axis with respect to thigh link 56.

Thigh link 56 attaches to the user's leg by a thigh panel 58. Thigh link 56 couples to thigh panel 58 at a joint 74. In one embodiment, joint 74 is an adjustable fixed joint to accommodate different users. In another embodiment, joint 74 includes a prismatic joint or slip joint that permits translation of thigh link 56 along the y-axis with respect to thigh panel 58. As prismatic joint, joint 74 absorbs vertical translation of thigh link 56 and corrects for misalignment of system joint 30 to the user's hip joint. Joint 74 reduces wear and abrasion on user 12 and further reduces error in compliant joint actuation system 10. Thigh panel 58, thigh link 56, and lever 32, including inner lever 32b and outer lever 32a, rotate together with respect to system joint 30. Thigh panel 58 comprises a primary interface between compliant actuation assembly 20 and the user's leg, where a force or torque from compliant actuation assembly 20 is transmitted to user 12. Thigh link 56, thigh panel 58, and joint 74 allows compliant joint actuation system 10 to efficiently transfer torque to user's hip joint.

Figure 4A:
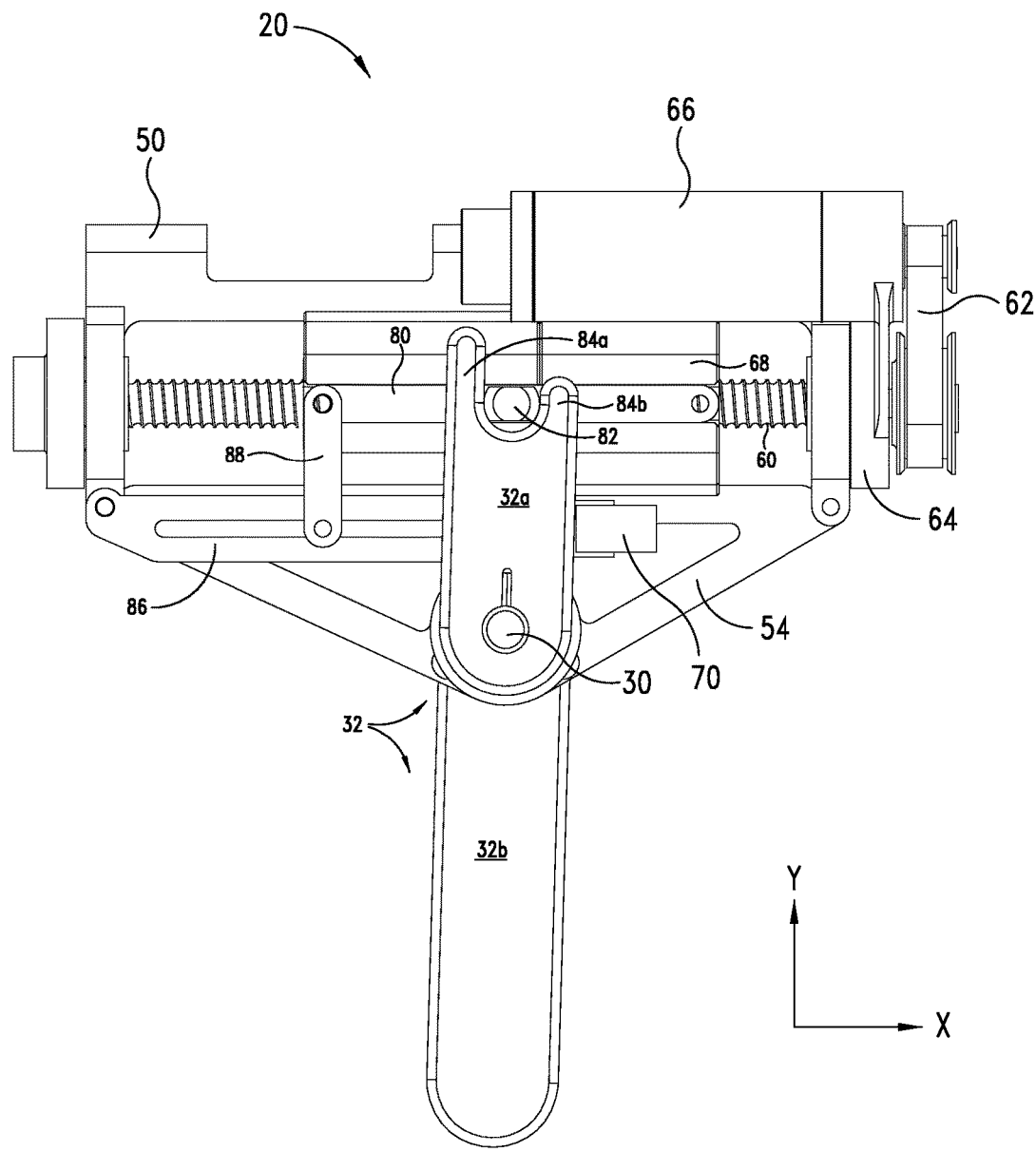
FIGS. 4a-4d illustrate a compliant actuation assembly for a joint actuation system.

FIGS. 4a-4d show additional detail of compliant actuation assembly 20. FIG. 4a shows a lateral side of compliant actuation assembly 20 for the right hip. Lever 32, including outer lever 32a and inner lever 32b, interfaces with compliant actuation assembly 20 at a spring push link 80. In one embodiment, spring push link 80 includes one or more protrusions or pins 82, and lever 32 includes a plurality of forks or prongs 84a-84b. Prongs 84a-84b are configured to engage and disengage with pin 82. Lever 32 engages and disengages from spring push link 80 by prongs 84a-84b of lever 32 moving in and out of proximity with a pin 82. In one embodiment, spring push link 80 includes a pin 82 on a medial and a lateral side of compliant actuation assembly 20. Each of inner lever 32a and outer lever 32b include prongs 84a-84b. Outer lever 32a interfaces with a pin 82 disposed on a lateral side of spring push link 80. On an opposite side of compliant actuation assembly 20, inner lever 32b interfaces with a pin 82 disposed on a medial side of spring push link 80.

Lever 32 is engaged with compliant actuation assembly 20 when pin 82 is positioned between prongs 84a-84b of lever 32. Prongs 84a-84b include a posterior prong 84a and an anterior prong 84b. When pin 82 is positioned between prongs 84a-84b, lever 32 is engaged. A space or distance between anterior prong 84b and posterior prong 84a is greater than a diameter of pin 82 to allow a gap between pin 82 and prongs 84a-84b. In one embodiment, a distance between anterior prong 84b and posterior prong 84a is 4 millimeters (mm) greater than a diameter of pin 82, thereby providing a 2 mm gap on either side of pin 82. The gap between pin 82 and prongs 84a-84b provide for error tolerance in the system. Thus, prongs 84a-84b may make contact with pin 82, or pin 82 may be disposed within the gap between prongs 84a-84b without contacting either prong. In either position, lever 32 is engaged with compliant actuation assembly 20.

Lever 32 is configured to disengage from pin 82 of compliant actuation assembly 20 when the user flexes the hip beyond a selected angle. Posterior prong 84a has a greater length than a length of anterior prong 84b. The length of anterior prong 84b allows anterior prong 84b to disengage with pin 82 when the user's leg flexes forward beyond a supported angle. Lever 32 is disengaged when pin 82 moves out from between prongs 84a-84b. A length of posterior prong 84a is configured to re-engage with pin 82, when user 12 extends leg 16 back from a flexed position. Where prongs 84a-84b move out of engagement with pin 82 during hip flexion beyond a torque-supported angle, posterior prong 84a catches pin 82 once user 12 moves leg 16 back within the torque-supported range. Thus, prongs 84a-84b are configured to engage with pin 82 to provide torque-support during gait activities and to disengage from pin 82 to provide unencumbered range of motion during non-gait activities. Lever 32 is further configured to remain engaged with pin 82 during hip extension. The length of posterior prong 84a ensures posterior prong 84a remains engaged with pin 82 when the user's leg extends backwards.

As user 12 moves leg 16, lever 32 moves with leg 16 and one of prongs 84a-84b may contact pin 82 to apply a force to pin 82. When prong 84a or 84b contacts pin 82 and applies force to pin 82, spring push link 80 is pushed in the direction of force on pin 82 along the x-axis. Spring push link 80 slides or translates along the length of screw 60. Spring push link 80 interfaces with support shell 68 by a sliding joint, such that spring push link 80 translates along the x-axis with respect to support shell 68. Spring push link 80 is coupled to one or more springs within support shell 68, with the springs shown in FIG. 4b. In FIG. 4a, support shell 68 encloses the springs. In one embodiment, one or more sensors 70 are coupled to spring push link 80 to measure spring deflection. Sensor 70 is coupled to lower bracket 54 by a sensor mount 86, and sensor mount 86 is coupled to spring push link 80 by a spring sensor link 88.

Figure 4C:
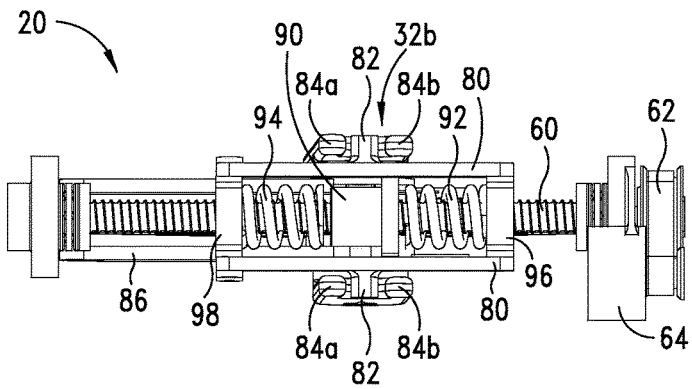
Figure 4B:
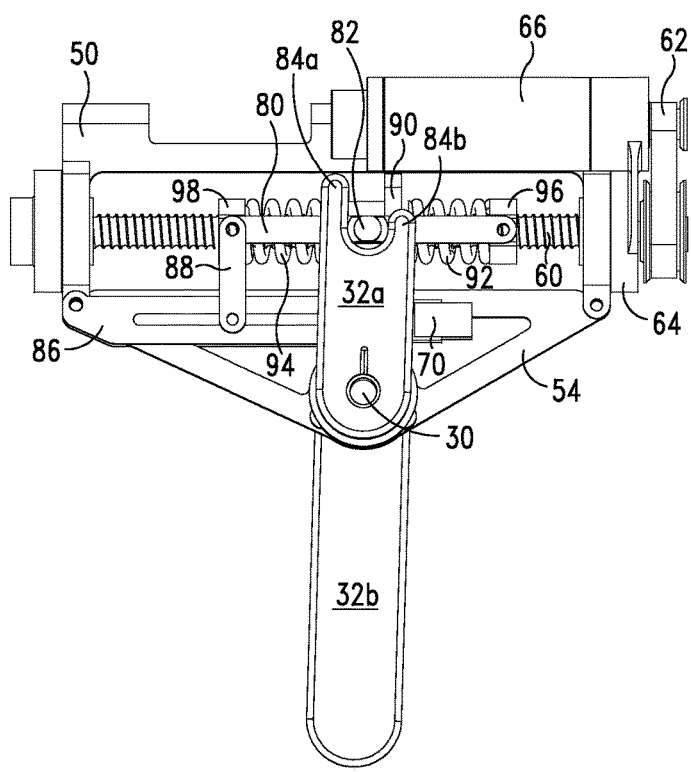

Support shell 68 also encloses a nut 90 coupled to support shell 68, with nut 90 shown in FIG. 4b. Actuator 66, belt 62, and screw 60 together operate to position nut 90. Support shell 68 couples to nut 90 by a rigid joint. Support shell 68 prevents nut 90 from rotating when screw 60 rotates, thereby forcing nut 90 to translate along the length of screw 60. As nut 90 translates along the length of screw 60, support shell 68 moves with the nut along the x-axis. A position of support shell 68, shown in FIG. 4a, corresponds to a position of nut 90, shown in FIG. 4b.

FIG. 4b shows the lateral side of compliant actuation assembly 20 for the right hip without support shell 68, thereby showing internal components of compliant actuation assembly 20. Within support shell 68, a nut 90 is threaded onto screw 60. Rotary power produced by actuator 66 is converted to linear power through the interface between screw 60 and nut 90. Nut 90 may include a ball screw, a roller screw, a plain screw, or other suitable component. In one embodiment, nut 90 includes a ball screw with a pitch of 2 mm and a diameter of 8 mm. As actuator 66 drives belt 62, screw 60 rotates while nut 90 does not rotate, thereby translating nut 90 linearly along screw 60.

Nut 90 translates independently of spring push link 80, and interfaces with spring push link 80 by contacting an anterior spring 92 or a posterior spring 94. Springs 92 and 94 are disposed around screw 60 and in line with nut 90, and thus, are configured to contact nut 90. Springs 92 and 94 may each include a helical, coil, or torsional spring, a leaf spring, a cable having elastic properties, or another type of compliant element or combination of compliant elements. In one embodiment, springs 92 and 94 are configured to operate in compression. Spring push link 80 includes a spring push cap at each end of spring push link 80. Spring push link 80 couples between an anterior spring push cap 96 and a posterior spring push cap 98. Spring push link 80 together with spring push caps 96 and 98 comprise a rigid structure. Anterior spring 92 is coupled to an anterior spring push cap 96, and posterior spring 94 is coupled to a posterior spring push cap 98. As lever 32 pushes on pin 82 of spring push link 80, the assembly of spring push link 80, spring push caps 96 and 98, and springs 92 and 94 move together along the axis of screw 60. Springs 92 and 94 remain at an uncompressed free length until compressed between nut 90 and a spring push cap 96 or 98. A position of nut 90 and lever 32 determines the compression in springs 92 and 94. Thus, lever 32 can be moved to compress a spring against nut 90, or nut 90 can be moved to compress a spring against a spring push cap, or nut 90 and lever 32 can both be moved to compress a spring between nut 90 and a spring push cap.

FIG. 4c shows a top view of compliant actuation assembly 20 without support shell 68, upper bracket 50, and actuator 66 in order to show springs 92 and 94 and nut 90. In FIG. 4c, springs 92 and 94 are shown at free length and not in contact with nut 90. Anterior spring 92 is mounted to anterior spring push cap 96, and posterior spring 94 is mounted to posterior spring push cap 98. Nut 90 translates along screw 60 independently of the assembly of spring push link 80, spring push caps 96 and 98, and springs 92 and 94.

To illustrate the relationship of the components within compliant actuation assembly 20, consider a movement of nut 90 with respect to springs 92 and 94 when user 12 is standing still. When user 12 is standing still, the user's leg 16 holds lever 32 in a fixed position. If actuator 66 moves nut 90 toward anterior spring 92, nut 90 applies a force to anterior spring 92. Anterior spring 92 pushes against anterior spring push cap 96 and moves anterior spring push cap 96 (together with spring push link 80, posterior spring push cap 98, and posterior spring 94) in the anterior direction until pin 82 contacts anterior prong 84b of lever 32. With lever 32 in a fixed position, anterior prong 84b holds pin 82, thereby preventing spring push link 80 and spring push caps 96 and 98 from moving in the anterior direction. As nut 90 continues to move in the anterior direction, anterior spring push cap 96 holds one end of anterior spring 92 in place, and nut 90 continues to compress anterior spring 92. Meanwhile, nut 90 has moved away from posterior spring 94 and posterior spring push cap 98, so posterior spring 94 remains at free length. Conversely, if actuator 66 moves nut 90 toward posterior spring 94, posterior spring 94 is compressed between posterior spring push cap 98 and nut 90 in a similar manner as described with respect to the anterior direction, while anterior spring 92 remains at free length.

To further illustrate the relationship of the components within compliant actuation assembly 20, consider a user 12 moving the leg 16 while the actuator 66 holds nut 90 in a fixed position on screw 60. When user 12 flexes at the hip to move leg 16 forward, lever 32 rotates about system joint 30 in a counterclockwise direction with respect to FIG. 4b, thereby moving prongs 84a-84b in a posterior direction, which is to the left in the view in FIG. 4c. The gap between pin 82 and prongs 84a-84b allow prongs 84a-84b to move freely for a short distance until a prong 84a or 84b contacts pin 82. With prongs 84a-84b moving in the posterior direction, anterior prong 84b comes into contact with pin 82 and exerts a force on pin 82 in the posterior direction. As pin 82 (together with spring push link 80, push caps 96 and 98, and posterior spring 94) moves in the posterior direction, anterior spring push cap 96 exerts a force on anterior spring 92. With nut 90 held in a fixed position, anterior spring push cap 96 compresses anterior spring 92 against nut 90. Meanwhile, posterior spring push cap 98 has moved away from nut 90, so posterior spring 94 remains at free length. Conversely, if user 12 extends at the hip to move leg 16 backwards, lever 32 rotates in a direction that moves prongs 84a-84b to the right in FIG. 4c, and posterior spring 94 is compressed between posterior spring push cap 98 and nut 90 in a similar manner as described with respect to hip flexion, while anterior spring 92 remains at free length.

Consider the interaction of the components where nut 90 is controlled during the user's gait to follow the movement of lever 32. For example, the angle of the hip joint is measured by disposing a sensor 70 on system joint 30. The angle of system joint 30 corresponds to the path of lever 32 as lever 32 follows the user's leg 16 through a gait cycle. Where actuator 66 is given a command to match or follow the path of lever 32, actuator 66 rotates screw 60 to move nut 90 back and forth according to the detected hip angle. When user 12 flexes at the hip to move leg 16 forward, lever 32 rotates to move prongs 84a-84b in a posterior direction. Meanwhile, actuator 66 moves nut 90 in a posterior direction, thereby pushing on posterior spring 94, posterior spring push cap 98, and ultimately pin 82. Nut 90, springs 92 and 94, spring push caps 96 and 98, and spring push link 80 move together without compressing either spring. With nut 90 and pin 82 moving in the same direction and at the same speed as prongs 84a-84b, pin 82 follows within the gap of prongs 84a-84b. Prongs 84a-84b do not exert a force on pin 82, and thus, lever 32 does not hold spring push cap to cause compression in a spring. Springs 92 and 94 remain at free length. Where nut 90 matches the speed of lever 32, pin 82 remains between prongs 84a-84b with a gap on either side of pin 82. The gap provides for error tolerance of the system, allowing the position of nut 90 to be slightly off, without the user feeling resistance from the system. Springs 92 and 94 provide additional error tolerance, by absorbing force and smoothing the impact of force on user 12. User 12 experiences a more gradual or natural force, rather than a jolting force from compliant joint actuation system 10.

Figure 4D:
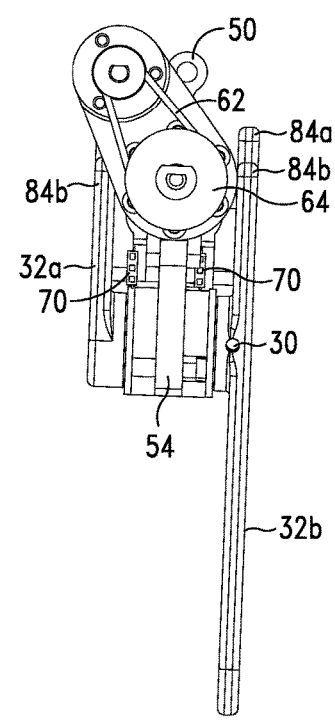

FIG. 4d shows a front view of compliant actuation assembly 20. The configuration of compliant actuation assembly 20 reduces torque loss, thereby reducing the length of the motor stroke required to accomplish a desired force output. Actuator 66 is smaller and faster than an actuator needed for systems with a longer motor stroke. In one embodiment, actuator 66 includes a brushless direct current (DC) 4-pole, 22 mm, 90 watt (W) motor and belt drive assembly 62 includes a 2.5:1 gear ratio. Belt drive assembly 62 allows the screw-drive to operate at lower speeds, such as for a walking gait speed. Compliant actuation assembly 20 is more compact and lighter in weight.

Compliant joint actuation system 10 may include a plurality of sensors 70 disposed on compliant actuation assembly 20. In one embodiment, sensors 70 include a motor encoder on actuator 66, an angular position sensor on system joint 30, and one or more sensors to measure deflection in springs 92 and 94. A motor encoder on actuator 66 measures a position of actuator 66 to determine a position of nut 90 and is used for a closed-loop control of nut 90. An angular position sensor on system joint 30 includes an absolute-style potentiometer that measures the position of joint 30 for determining the user's hip position. In one embodiment, two position sensors are used to measure deflection in springs 92 and 94. One of sensors 70 includes a first potentiometer coupled to an end of spring 92 or 94, for example, at an end of spring push link 80 by spring sensor link 88, shown in FIG. 4b. Another of sensors 70 includes a second potentiometer coupled to nut 90 by nut sensor link 72 coupled to support shell 68, shown in FIG. 3b. As nut 90 moves relative to spring push link 80, nut sensor link 72 moves relative to spring sensor link 88. A position of spring sensor link 88 and nut sensor link 72 are measured by the first and second potentiometers, respectively. As the position of nut 90 and spring push link 80 deviates, the difference in the signals from the potentiometers reflects the deviation in position. The distance between the positions of nut 90 and spring push link 80 correlates to deflection in spring 92 or 94. Thus, deflection in springs 92 and 94 are measured using a plurality of position sensors, such as potentiometers. In another embodiment, deflection in springs 92 and 94 is measured directly by a sensor 70 disposed on the springs. Alternatively, other types of sensors are used to measure motor position, the user's hip position, and spring deflection.

Figure 5A:
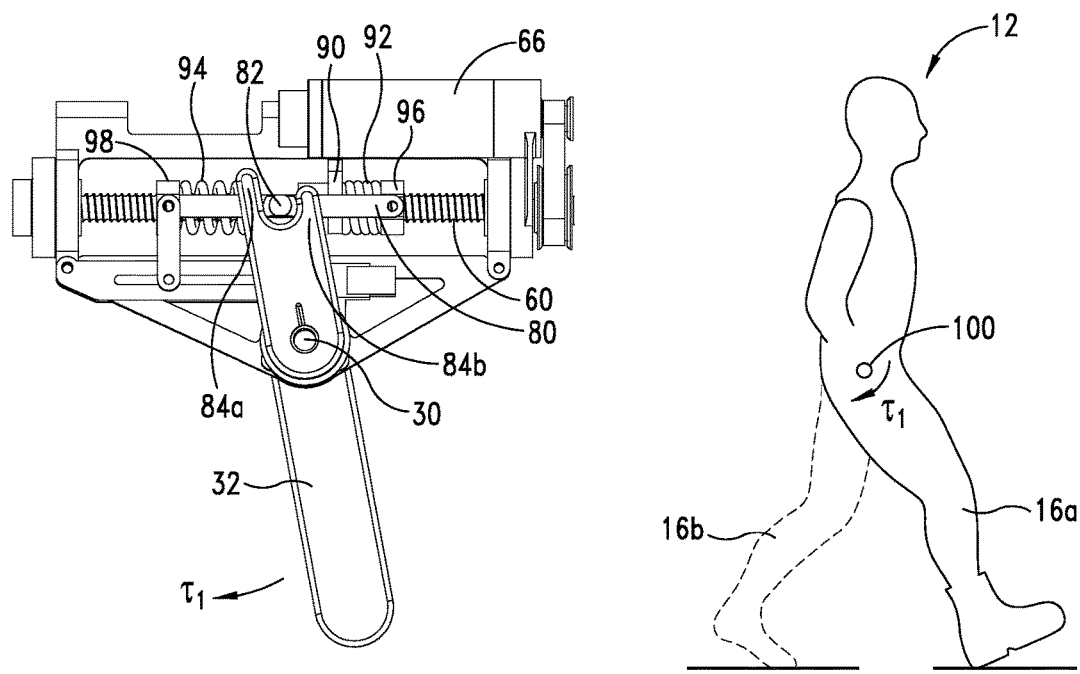
FIGS. 5a-5b illustrate a method of using a compliant joint actuation system.
Figure 5B:
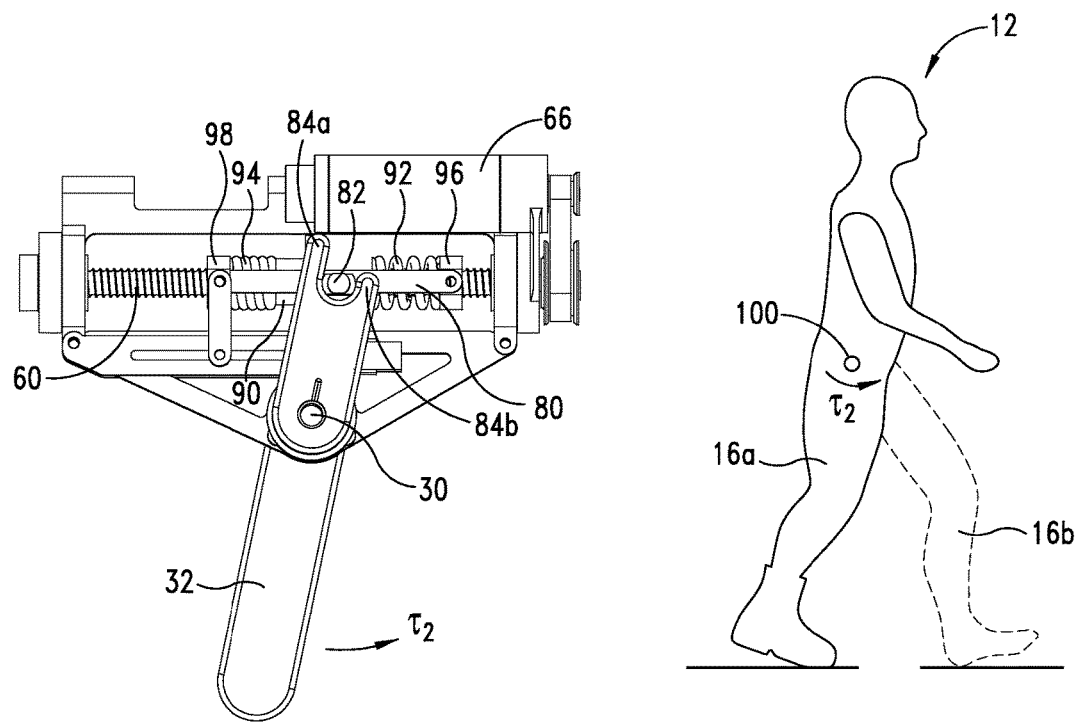

FIGS. 5a-5b show a method of using a compliant joint actuation system 10 and a schematic representation of a bi-directional compliant joint actuation system for a hip joint with a corresponding position of a user's gait cycle. The position of compliant actuation assembly 20 is described for a right-side compliant actuation assembly 20 worn at the user's right anatomical hip joint 100. A left-side compliant actuation assembly 20 is not shown for the gait of a left leg 16b, but operates similarly to the right side portion described with respect to FIGS. 5a-5b.

FIG. 5a shows the beginning of a gait cycle for a right leg 16a of user 12 as the right leg 16a enters stance phase. User 12 enters stance phase on the user's right side by making a heel strike with the right foot contacting the ground. Right leg 16a is flexed in a forward position in the sagittal plane. Lever 32 is rotated forward with right leg 16a, and prong 84b of lever 32 pushes pin 82 back in the posterior direction. Anterior spring 92 is compressed between nut 90 and anterior spring push cap 96. The movement of right leg 16a forward during swing phase causes compression of anterior spring 92, which is released back to user 12 during stance.

After heel strike, right leg 16a is flexed forward and right leg 16a changes direction to extend backward. Compliant joint actuation system 10 provides a torque $\tau_1$ at hip joint 100 as right leg 16a changes direction and enters stance phase. After right leg 16a reaches maximum flexion and begins to change direction and move backwards with respect to the user's hip joint, anterior spring 92 begins to un-compress and release the stored energy back to user 12. Anterior spring 92 pushes on anterior spring push cap 96 together with spring push link 80 and pin 82. The energy released from anterior spring 92 ultimately pushes on anterior prong 84b to apply a portion of total torque $\tau_1$ acting at system joint 30.

As user 12 extends the right hip and moves through stance phase, actuator 66 positions nut 90 to add deflection in anterior spring 92. The force from nut 90 adds compression in anterior spring 92, while anterior spring 92 pushes forward on anterior spring push cap 96, thereby adding more force at pin 82. The additional deflection added to anterior spring 92 by nut 90 during early stance creates additional torque, which is greater than torque provided by the loading of anterior spring 92 from the leg moving during swing. The total torque $\tau_1$ supplied by compliant actuation assembly 20 includes the torque resulting from the release of energy stored in anterior spring 92 by the user loading anterior spring 92 during swing phase. The total torque $\tau_1$ further includes the torque added by moving nut 90 to add deflection into anterior spring 92 during early stance phase. Thus, the position of actuator 66 increases a force or torque applied to right leg 16a by lever 32. The result of the force or torque applied by compliant joint actuation system 10 is a torque $\tau_1$ acting at hip joint 100. Torque $\tau_1$ is applied to user 12 in the sagittal plane in the direction of the arrow shown in FIG. 5a and assists user 12 with hip extension. A second compliant joint actuation system 10 is worn on left leg 16b to provide a torque, similar to torque $\tau_1$, acting on the left hip joint during stance phase of left leg 16b. Compliant joint actuation system 10 provide bi-directional torque support, by applying an assistive force or torque in a direction of hip extension during stance phase, as well as an assistive force or torque in a direction of hip flexion during swing phase.

FIG. 5b shows a late stance position during the gait of user 12. Compliant joint actuation system 10 provides a flexion torque $\tau_2$ at right hip joint 100 as right leg 16a enters swing phase. At the end of stance phase for the user's right leg 16a, right left 16a is extended backward and the right foot is about to lift from the ground. Lever 32 is rotated backward with right leg 16a, and prong 84a of lever 32 pushes pin 82 forward in the anterior direction. Posterior spring 94 is compressed between nut 90 and posterior spring push cap 98. The movement of right leg 16a backward during stance phase causes compression in posterior spring 94, which is released back to user 12 during swing.

The right hip is extended, and changes direction as user 12 begins to flex the right hip to swing right leg 16a forward. Compliant joint actuation system 10 provides a torque $\tau_2$ at hip joint 100 as right leg 16a changes direction and enters swing phase. After right leg 16a reaches maximum extension and begins to change direction and swing forward, posterior spring 94 begins to un-compress and release the stored energy back to user 12. Posterior spring 94 pushes on posterior spring push cap 98 together with spring push link 80 and pin 82. The energy released from posterior spring 94 ultimately pushes on posterior prong 84a to apply a portion of total torque $\tau_2$ acting at system joint 30.

As user 12 flexes the right hip and enters swing phase, actuator 66 positions nut 90 to add deflection in posterior spring 94. The force from nut 90 adds compression in posterior spring 94, while posterior spring 94 pushes back on posterior spring push cap 98, thereby adding more force at pin 82. The additional deflection added to posterior spring 94 by nut 90 during early swing creates additional torque, which is greater than torque provided by the loading of posterior spring 94 from leg 16a moving relative to hip joint 100 during stance. The total torque $\tau_2$ supplied by compliant actuation assembly 20 includes the torque resulting from the release of energy stored in posterior spring 94 by the user loading posterior spring 94 during stance phase. The total torque $\tau_2$ further includes the torque added by moving nut 90 to add deflection into posterior spring 94 during early swing phase. Thus, the position of actuator 66 increases a force or torque applied to right leg 16a by lever 32. The result of the force or torque applied by compliant joint actuation system 10 is a torque $\tau_2$ acting at hip joint 100. Torque $\tau_2$ is applied to user 12 in the sagittal plane in the direction of the arrow shown in FIG. 5b and assists user 12 with hip flexion. By providing torque $\tau_1$ and torque $\tau_2$ at the point the leg 16a changes direction of motion, compliant joint actuation system 10 enhances human motion and reduces the metabolic cost of gait.

Figure 6A:
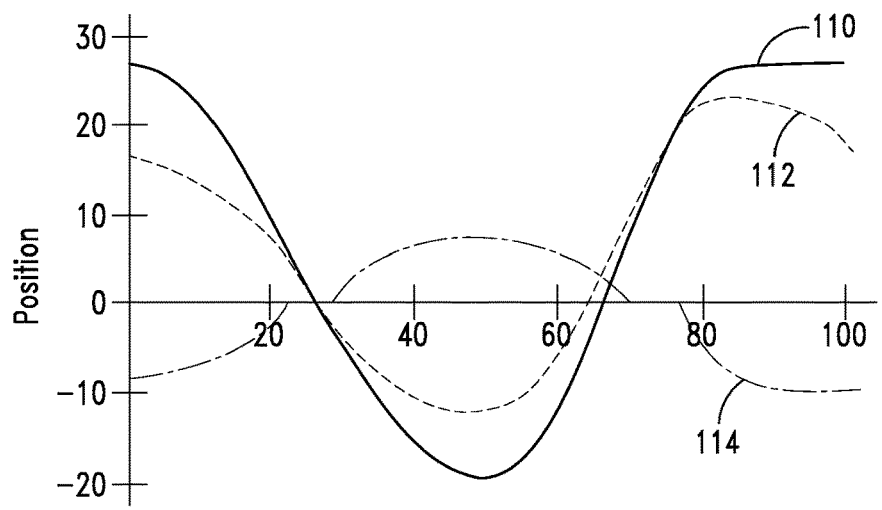
FIGS. 6a-6c illustrate graphs of the performance of a compliant joint actuation system for a hip joint.
Figure 6B:
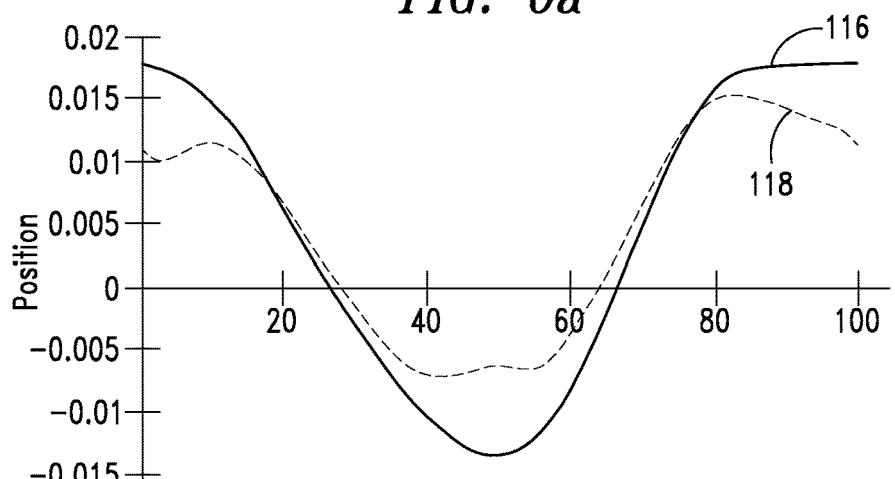
Figure 6C:
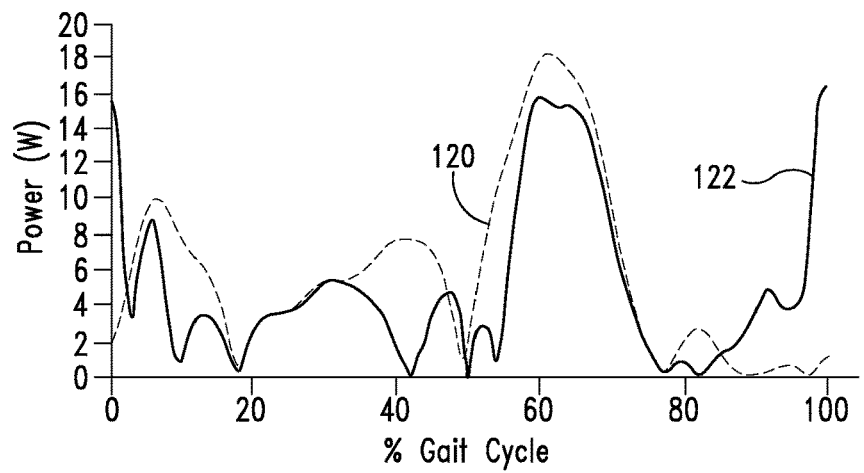

FIGS. 6a-6c show results of a motor controller for actuator 66. The x-axis of each graph shows a gait cycle in terms of percentage of a single gait cycle for one leg of user 12 beginning with a heel strike. For a walking gait speed, the first 60% of the gait cycle represents stance phase, while the remaining 60%-100% of the gait cycle represents swing phase. A position of the user's hip joint 100 relates to the position of the user's leg. Hip position is measured with respect to a neutral position, shown as 0 degrees on the y-axis in FIG. 6a. The user's leg changes direction at approximately 0% and 50% of the gait cycle.

FIG. 6a shows a graph of an example of a control pattern for compliant joint actuation system 10. The y-axis of the graph shows position measured in degrees (°) relative to a neutral position of leg 16. Line 110 shows an example of hip position for a user's hip joint 100 throughout a single gait cycle. A heel strike is represented at zero on the x-axis (0% of the gait cycle) and marks the beginning of stance phase and the beginning of a gait cycle. At heel strike, the user's leg 16 is flexed forward at the hip joint 100. From heel strike, the leg begins to extend backward to push the body over the foot. The negative slope of line 110 between 0%-50% of the gait cycle represents hip extension during stance. Approximately 30% of the gait cycle represents mid-stance, where the hip is in a vertically neutral position. At approximately 50% of the gait cycle, the hip is fully extended, shown at approximately −20°.

Line 112 shows an example of an ideal control pattern for nut 90 in order for compliant joint actuation system 10 to supply assistive torque at the hip joint during stance and swing phases of gait. The difference between line 110 and 112, or the area between lines 112 and 110 represents the deflection in springs 92 and 94. The deflection in springs 92 and 94 is also represented by a single line 114.

FIG. 6*b* shows a motor path for actuator 66 compared to a position of an end effector of compliant joint actuation system 10. Line 116 shows an example of an end effector position of compliant joint actuation system 10. In one embodiment, lever 32 operates as the end effector of compliant joint actuation system 10. The position of lever 32 corresponds to a position of the user's hip joint 100. Thus, line 116 resembles or matches a hip position, which is shown by line 110 in FIG. 6*a*. Line 118 in FIG. 6*b* represents an example of a desired path for actuator 66 to accomplish the end effector position of line 116. The difference between line 116 and 118 correlates to the deflection of springs 92 and 94. The deflection of springs 92 and 94 correlates to the torque, the supporting force, provided by compliant joint actuation system 10. A desired peak torque from compliant joint actuation system 10 is approximately 15 newton-meters (N·m).

FIG. 6*c* shows the difference in power at the end effector relative to the power provided by actuator 66. Line 120 shows the power output at lever 32 throughout a gait cycle, while line 122 shows the power required by actuator 66 to produce the end effector power output of line 120. The Maxon EC 4-pole 22 motor weighs 0.125 kilograms (kg) but still provides up to 90 watts (W) of continuous power, or 720 watts per kilogram (W/kg). For example, where springs 92 and 94 each have a stiffness k of 72,502 newtons per meter (N/m), peak motor power is 16.8 W, with a 4.9 W continuous average. A motor power requirement can be represented as a function of the difference between power needed for gait and power contribution from a compliant element, as shown by equation (1).

$$P_m = F \cdot \dot{x} - \frac{F \cdot \dot{F}}{k} \quad (1)$$

Where: $P_m$=motor power
F=linear force acting on the spring
$\dot{x}$=velocity of the end effector
k=spring stiffness As seen in equation (1), the first term is a representation of the output power required for gait and that the second term represents the power contribution of the spring. By appropriately tuning the spring stiffness, the power input from the motor can be reduced. FIG. 6*c* shows the results of optimizing a spring stiffness to provide the peak torque of 15 N·m to the hip joint during walking.

Figure 8:
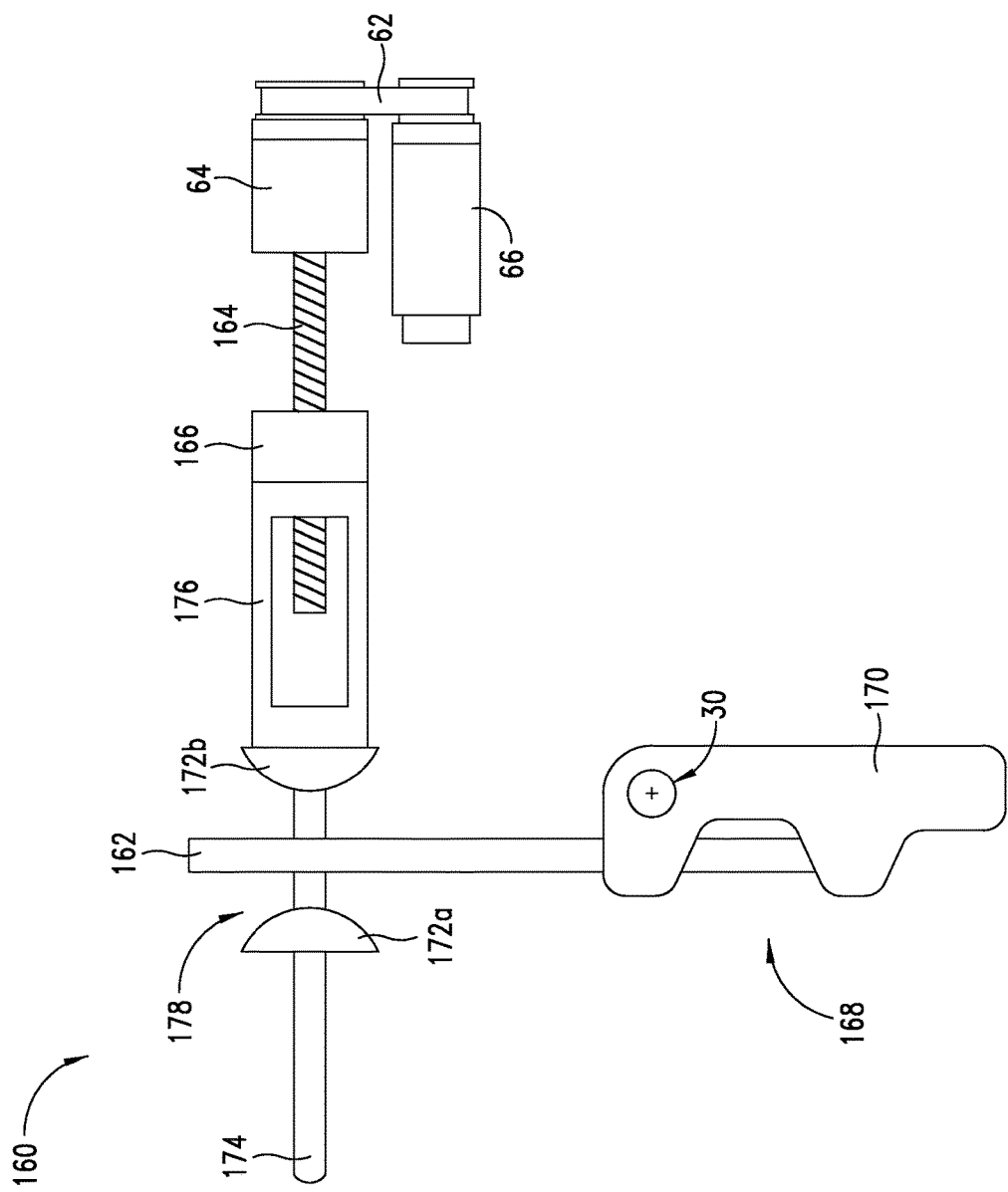
FIG. 8 illustrates another alternative compliant actuation assembly for a joint actuation system.

Alternative embodiments of compliant actuation assembly 20 can include substitutions of the individual components to achieve the compliant actuation functionality. Actuator 66 can be electrical, hydraulic, or pneumatic in nature. Belt drive assembly 62 can be accomplished by use of any gear reduction approach including rollers, toothed gear assemblies in single or multiple stages, or a combination of gear assemblies. Alternatively, the gear reduction is optional and the motor element, such as actuator 66, can be directly coupled to the screw shaft assembly, such as screw 60. The screw nut assembly, such as screw 60 and nut 90, can be based on a sliding friction-style screw, ball screw, or roller screw arrangement. The compliant or spring element, such as springs 92 and 94, can be substituted with one or more compliant elements. For example, a single spring operating in both tension and compression may be used in place of the two compression springs. The compliant or spring element can be substituted with other types of compliant elements, such as rubber, polymer, or flexural elements. For example, compliant actuation assembly 20 may include a leaf spring arrangement as shown in FIG. 8.

Figure 7:
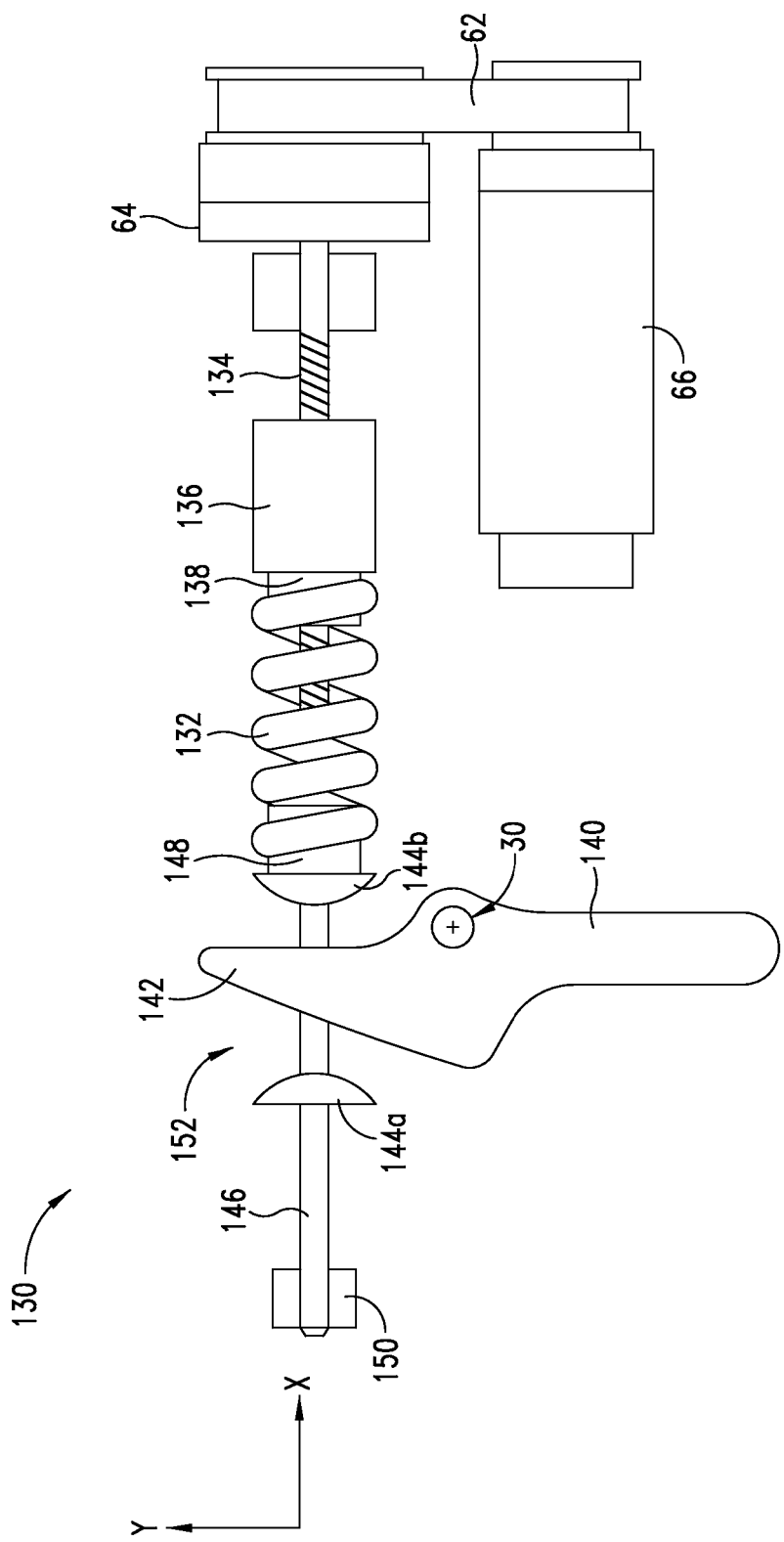
FIG. 7 illustrates an alternative compliant actuation assembly for a joint actuation system.

FIG. 7 shows an alternative embodiment of a compliant actuation assembly for a compliant joint actuation system. Compliant actuation assembly 130 is similar to compliant actuation assembly 20, but implements the compliant actuation using a single coil spring 132. Spring 132 is configured to operate in tension and compression. Compliant actuation assembly 130 includes a motor-driven screw 134, which is coupled to a belt 62 by a bracket 64 and which is coupled to an actuator 66. Bracket 64 includes a bearing assembly for converting the motion of actuator 66 and belt 62 to drive screw 134. Screw 134 rotates to translate a nut 136 according to a control pattern, for example, as described with respect to FIG. 6*a*. Actuator 66 is controlled by control system 34 from FIG. 1. Nut 136 couples to spring 132 by a link or joint 138 that holds one end of spring 132 to nut 136.

Compliant actuation assembly 130 includes a lever 140 with a single prong 142, which interfaces with spring 132 and nut 136 through bumpers 144*a*-144*b* disposed on each side of prong 142. Bumpers 144*a*-144*b* are coupled to an end of spring 132 opposite to nut 136. In one embodiment, bumpers 144*a*-144*b* are disposed on a rigid shaft 146, and bumpers 144*a*-144*b* may be rigid or compliant. Shaft 146 is coupled to the end of spring 132 by a link or joint 148. Shaft 146 is further coupled to a mounting bracket by a bearing 150. Bearing 150 may include a plain bearing that holds shaft 146 in place with respect to the y-axis, while allowing shaft 146 to slide along the x-axis.

Lever 140, bumpers 144*a*-144*b*, and spring 132 of compliant actuation assembly 130 operate similarly to lever 32, prongs 84*a*-84*b*, pin 82, and springs 92 and 94 of compliant actuation assembly 20 to provide bi-directional torque. A position of nut 136 and lever 140 determines the tension or compression in spring 132. Prong 142 of lever 140 applies force to bumper 144*b* to compress spring 132 against nut 136, or prong 142 of lever 140 applies force to bumper 144*a* to pull on spring 132 to add tension into spring 132. Additionally, nut 136 is positioned to change the deflection in spring 132. A position of both nut 136 and lever 140 determine the deflection of spring 132. Screw 164 rotates to translate nut 166 according to a control pattern, for example, as described for compliant actuation assembly 20. Actuator 66 is controlled by control system 34 as described herein. A gap 152 available between bumpers 144*a*-144*b* and lever 140. Gap 152 ensures lever 140 is able to disengage from bumpers during hip flexion beyond a supported range. Gap 152 also provides error tolerance for actuator 66.

A mounting bracket for compliant actuation assembly 130 may be similar to upper bracket 50 and/or lower bracket 54 as shown for compliant actuation system 20 (see FIG. 4a). Lever 140 couples to a mounting bracket at system joint 30. Lever 140 further couples to a leg attachment assembly 22 from FIG. 1. Lever 140 rotates about the system joint 30 similarly to lever 32 from compliant actuation assembly 20. The resulting force or torque applied by compliant actuation assembly 130 at system joint 30 is transferred to the user's hip joint 100 by lever 140.

FIG. 8 shows another embodiment of a compliant actuation assembly for a compliant joint actuation system 10. Compliant actuation system 160 is similar to compliant actuation assemblies 20 and 130, but implements the compliant actuation using a leaf spring 162. Compliant actuation assembly 160 includes a motor-driven screw 164, which is coupled to a belt 62 by a bracket 64 and which is coupled to an actuator 66. Bracket 64 includes a bearing assembly for converting the motion of actuator 66 and belt 62 to drive screw 164. Screw 164 rotates to translate a nut 166 along screw 164 according to a control pattern, for example, as described with respect to compliant actuation assembly 20. Compliant actuation assembly 160 includes a lever 168 comprising a rigid link 170 and leaf spring 162. Leaf spring 162 may include a singular leaf spring or leaf spring stack and may further include additional compliant elements. Rigid link 170 holds leaf spring 162, and rotates with respect to system joint 30. Leaf spring 162 of lever 168 interfaces with bumpers 172a-172b disposed on each side of leaf spring 162. Bumpers 172a-172b may be rigid or compliant. In one embodiment, bumpers 172a-172b are disposed on a rigid shaft 174. Bumpers 172a-172b and shaft 174 are coupled to nut 166 by a link 176. A position of nut 166 determines a position of link 176, bumpers 172a-172b, and shaft 174, which together translate along the axis of screw 164. Shaft 174 is optionally coupled to a mounting bracket by a bearing at an end of shaft 174 opposite to nut 166. Shaft 174 is rigidly affixed with respect to the y-axis, and shaft 174 slides along the x-axis by operation of nut 166.

Lever 168 and bumpers 172a-172b of compliant actuation assembly 160 operate similarly to lever 32, prongs 84a-84b, pin 82, and springs 92 and 94 of compliant actuation assembly 20 to provide bi-directional torque. A position of nut 166 and lever 168 determines the deflection in leaf spring 162. Leaf spring 162 contacts bumper 172b to deflect leaf spring 162 in a first direction, and leaf spring 162 contacts bumper 172b to deflect leaf spring 162 in a second direction. Additionally, nut 166 is positioned to move bumpers 172a-172b to change the deflection in leaf spring 162. A position of both nut 136 and leaf spring 162 determine the deflection of leaf spring 162. A gap 178 is available between bumpers 172a-172b and leaf spring 162. Gap 178 ensures leaf spring 162 is able to disengage from bumpers during hip flexion beyond the supported range. Gap 152 also provides error tolerance for actuator 66.

A mounting bracket for compliant actuation assembly 160 may be similar to upper bracket 50 and/or lower bracket 54 as shown for compliant actuation system 20 (see FIG. 4a). Lever 168 couples to a mounting bracket at system joint 30. Lever 168 further couples to a leg attachment assembly 22 from FIG. 1. Lever 168 rotates about the system joint 30 similarly to lever 32 from compliant actuation assembly 20. The resulting force or torque applied by compliant actuation assembly 160 at system joint 30 is transferred to the user's hip joint 100 by lever 168.

Compliant actuation assembly 160 shown in FIG. 8 is the similar to compliant actuation assembly 130 shown in FIG. 7. A difference is that coil spring 132 shown in FIG. 7 is replaced by a rigid tube 176 in FIG. 8 and the upper portion of the rotary lever 140 in FIG. 7 is replaced by a singular leaf spring 162 or leaf spring stack. The leaf spring arrangement in FIG. 8 would be operationally equivalent to the configuration shown in FIG. 7. Both FIG. 7 and FIG. 8 describe an actuation approach that is bi-directional in the application of torque and includes the addition of an operational gap 152 or 178. In both cases, the design approaches can be modified to become unidirectional in operation and/or operate with or without a gap. The use of the gap in the control scheme offers robustness and error tolerance to the interface with the device user. The use of the gap minimizes the level of performance bandwidth the controlled motor response requires to serve user 12 without interference. By contrast, a direct coupling of the linkages to the lever without a gap would involve low error tolerance and would be too reactive to small movements of a user. The combination of system compliance and a physical gap gives the controller time to smoothly react to the needs of the system wearer. The response time made available by the gap reduces both the potential device interference to the user as well as the amount of power used to provide torque assistance.

Figure 9:
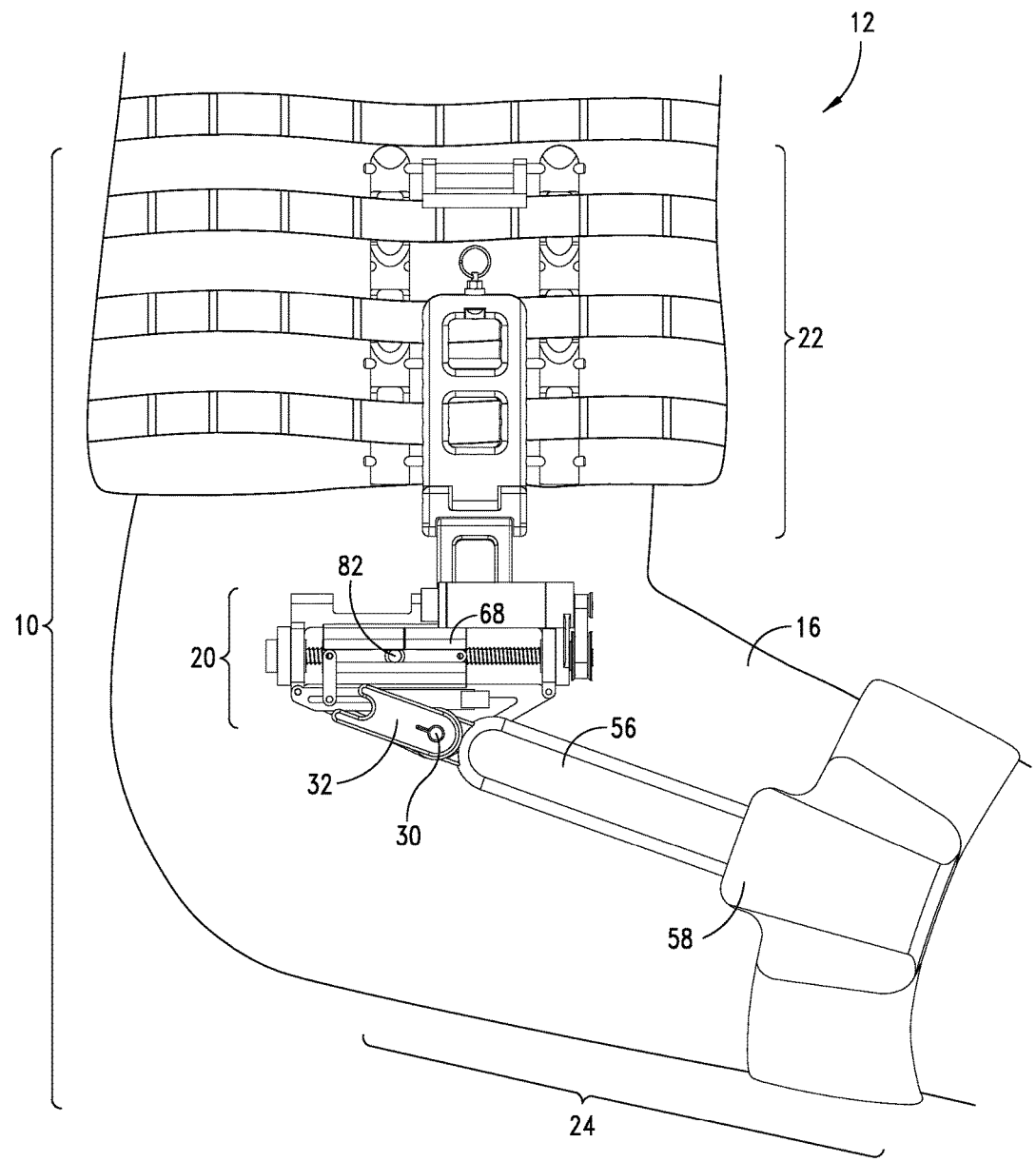
FIG. 9 illustrates a compliant joint actuation system in a disengaged position.

FIG. 9 shows compliant joint actuation system 10 in a disengaged position. User's leg 16 is shown in a flexed position. For example, when user 12 sits in a chair, steps up an incline or a stair, or bends down, the angle of the hip flexes past the supported angle of compliant actuation assembly 20. When leg 16 flexes past a supported angle of rotation, lever 32 disengages from pin 82 by moving out of a range where prongs of lever 32 can reach pin 82. Support shell 68 represents a nut position, and pin 82 represents a position of springs 92 and 94. Support shell 68 and pin 82 move back in the posterior direction until reaching a maximum supported position. Lever 32 moves out of engagement with pin 82. When pin 82 is no longer between the prongs of lever 32, compliant actuation system 20 is disengaged. Actuator 66 holds a position of the nut and support shell 68 ready to reengage when lever 32 moves back into the supported range of motion. Thus, while user 12 is performing a non-gait activity, the system is ready to re-engage upon user 12 resuming a gait activity.

In one embodiment, compliant joint actuation system 10 includes a forked lever 32 that will naturally disengage from the screw mechanism once the hip flexion range of motion exceeds that of a normal walking gait. By disengaging lever 32 user 12 is enabled to have free and unrestricted movement while performing tasks other than walking. While wearing system 10 and not walking, such as when sitting or standing, nut 90 can be driven to maintain a specified gap, allowing the user's hip joint to be free of resistance from the system. Lever 32 rotates completely out of engagement of compliant actuation assembly 20. This feature allows the thigh to flex forward well beyond a normal walking range of motion. In this instance, the spring actuator will simply hold position, ready to receive lever 32 again, when normal assisted ranges of motion are resumed. The inclusion of a position sensor (encoder) at system joint 30 is used to determine a position of lever 32 and to determine if lever 32 is engaged or disengaged. The forked lever 32 includes a posterior prong with a greater length than an anterior prong. The length of the posterior prong ensures lever 32 catches pin 82 during hip extension in order to re-engage lever 32 with pin 82.

Figure 10B:
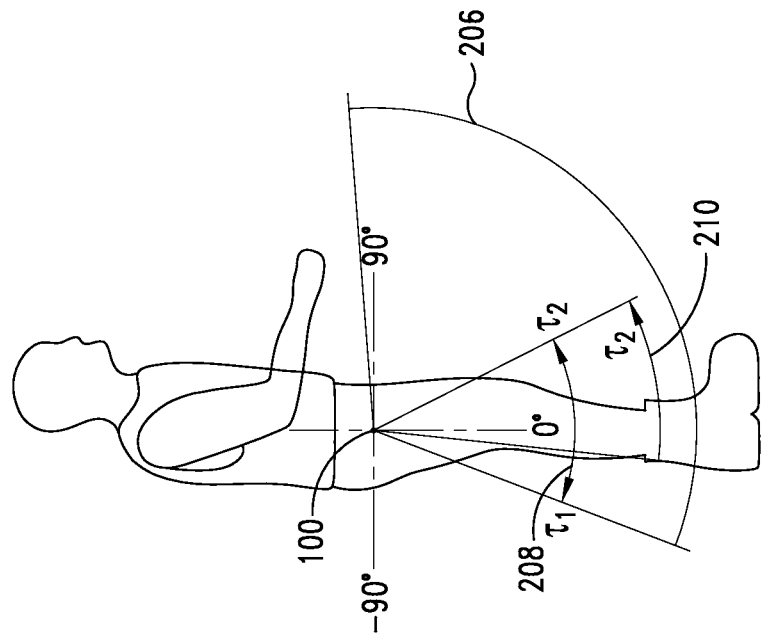
FIGS. 10a-10b illustrate a schematic representation of a range of motion for a compliant joint actuation system.
Figure 10A:
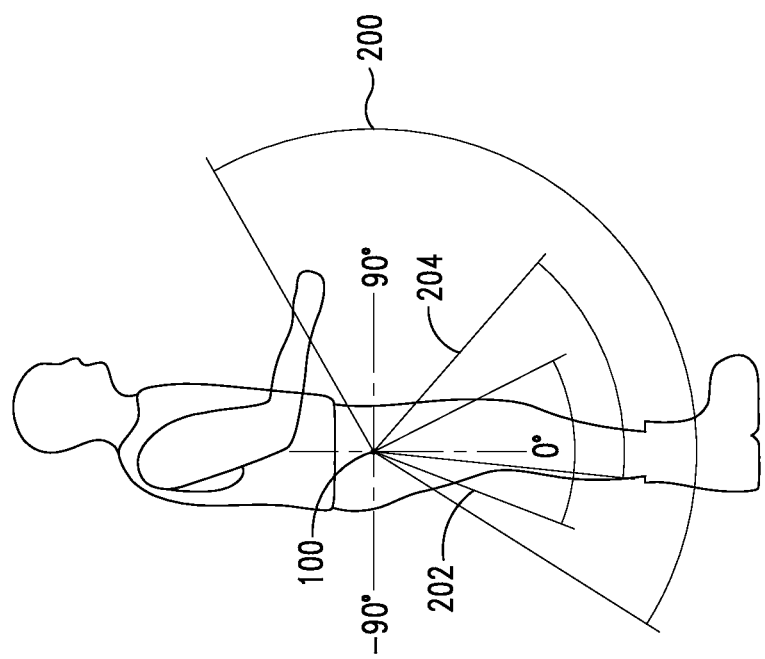

FIGS. 10a-10b show a range of motion for a compliant joint actuation system 10 compared to able-bodied range of motion. The range of motion of the hip joint is discussed in FIGS. 10a-10b with respect to a neutral position, indicated at 0° in the y-direction, or vertically downward with respect to anatomical hip joint 100. FIG. 10a shows an example of able-bodied range of motion. Area 200 shows a total range of motion of an anatomical hip joint 100. Total range of motion for an able-bodied hip is approximately 150°, with 120° of hip flexion and 30° of hip extension. Area 202 shows a typical range of motion of anatomical hip joint 100 during a walking gait speed. Total range of motion for able-bodied walking is approximately 47°, with 27° of hip flexion and 20° of hip extension, centered at 3.5°. Area 204 shows a typical range of motion of anatomical hip joint 100 during a running gait speed. Total range of motion for able-bodied running is approximately 55°, with 50° of hip flexion and 5° of hip extension, centered at 22.5°.

FIG. 10b shows a range of motion of a compliant joint actuation system 10. In one embodiment, compliant joint actuation system 10 is designed for a walking gait speed. For example, a configuration of compliant actuation assembly 20 is optimized to supply torque during walking, but also permits the user to run or to perform non-gait activities by allowing a range of unencumbered motion that is greater than a range of torque-supported motion. Area 206 shows a total range of motion of a system joint 30. Total range of motion for a system joint 30 is approximately 115°, with 95° of hip flexion and 20° of hip extension. Area 208 shows a range of motion of system joint 30 during a walking gait speed in which compliant joint actuation system 10 is able to supply an extension torque $\tau_1$ and a flexion torque $\tau_2$. Total range of motion through which system 10 can supply torque during a walking gait speed is approximately 47°, with 27° of hip flexion and 20° of hip extension, centered at 3.5°. Comparing area 208 with area 202 from FIG. 10a shows that the torque-supported walking range of motion for system 10 is equivalent to able-bodied walking range of motion.

Area 210 shows a range of motion of system joint 30 during a running gait speed in which compliant joint actuation system 10 is able to supply a flexion torque $\tau_2$. Total range of motion through which system 10 can supply a flexion torque $\tau_2$ during a running gait speed is approximately 32°, with 27° of hip flexion and 5° of hip extension, centered at 11°. Comparing area 210 with area 204 from FIG. 10a shows that a system 10 designed for walking is also able to support a substantial range of hip flexion during running.

FIGS. 11a-11b show an alternative embodiment of a compliant actuation assembly for a compliant joint actuation system 10. FIG. 11a shows a compliant actuation assembly 220 configured to support an enhanced range of motion. Compliant actuation assembly 220 is similar to compliant actuation assembly 20, but implements the compliant actuation using a single spring 222 with a rack 224 and pinion 226. In one embodiment, rack 224 includes a plurality of pins 228 and pinion 226 includes a partial sprocket. Rack 224 includes at least one pin 228 and may include any number of pins 228. In one embodiment, rack 224 includes two pins 228. Pinion 226 includes a plurality of teeth 230 that interface with pins 228 of rack 224. A greater number of pins 228 increases the power stroke of compliant actuation assembly 220.

Pinion 226 further includes a lever arm 232 that couples to the user's leg by a leg attachment assembly 22 from FIG. 1. Lever arm 232 is engaged with compliant actuation assembly 220 when a pin 228 from rack 224 is positioned between teeth 230 of pinion 226. Pinion 226 and lever arm 232 rotate about a system joint 30 similarly to lever 32 from compliant actuation assembly 20. Lever arm 232 corresponds to a position of the user's leg, and the torques produced at system joint 30 are transmitted to the user's hip joint.

A position of rack 224 is controlled by a motor-driven screw 234. Screw 234 rotates to translate a nut 236, which is coupled to one end of spring 222 by a link or joint 238. Rack 224 is coupled to an end of spring 222 opposite to nut 236 such that spring 222 is disposed between nut 236 and rack 224. Nut 236 is threaded onto screw 234, which is driven by an actuator 66 with a belt drive assembly 62. Rotary power produced by actuator 66 is converted to linear power through the interface between screw 234 and nut 236. Nut 236 is configured to translate along screw 234 when screw 234 is rotated.

FIG. 11b shows pinion disengaged from rack. When leg 16 flexes past a supported angle of rotation, pinion 226 disengages from rack 224 by moving out of a range where teeth 230 of pinion 226 can reach pins 228 of rack 224. Compliant actuation assembly 220 will naturally disengage once the hip flexion range of motion exceeds the designed range. When teeth 230 are no longer engaged between the pins 228, compliant actuation assembly 220 is disengaged. Pinion 226 can disengage from rack 224 by a movement of the user out of range of rack 224. Additionally, nut 236 may position rack 224 out of range of pinion 226 at each end of the user's range of motion and at each of the motor stroke. By disengaging pinion 226 from rack 224, user 12 is able to have free and unrestricted movement while performing tasks other than a gait activity. Actuator 66 holds a position of nut 236 ready for teeth 230 to reengage with rack 224 when pinion 226 moves back into the supported range of motion. Thus, while user 12 is performing a non-gait activity, the system is ready to re-engage upon user 12 resuming a gait activity.

FIGS. 12a-12b show a range of motion for a compliant joint actuation system with compliant actuation assembly 220 compared to able-bodied range of motion. The range of motion of the hip joint is discussed in FIGS. 12a-12b with respect to a neutral position, indicated at 0° in the y-direction, or vertically downward with respect to anatomical hip joint 100. FIG. 12a shows an example of able-bodied range of motion. Area 250 shows a total range of motion for an able-bodied hip is approximately 150°, with 120° of hip flexion and 30° of hip extension. Area 252 shows a typical range of motion for able-bodied walking is approximately 47°, with 27° of hip flexion and 20° of hip extension, centered at 3.5°. Area 254 shows a typical range of motion for able-bodied running is approximately 55°, with 50° of hip flexion and 5° of hip extension, centered at 22.5°. Area 256 shows a typical range of motion for able-bodied stair climbing is approximately 57°, with hip flexion in the range of 7° to 64°, centered at 35.5°.

FIG. 12b shows a range of motion of a compliant joint actuation system with compliant actuation assembly 220. In one embodiment, compliant actuation assembly 220 is designed for multiple gait speeds, such as walking and running. For example, a configuration of compliant actuation assembly 220 is optimized to supply torques at different hip angles for different gait speeds. Compliant joint actuation system 220 also permits the user to climb stairs or to perform non-gait activities by allowing a range of unencumbered motion that is greater than a range of torque-supported motion. Area 258 shows a total range of motion of a system joint 30. Total range of motion for a system joint 30 is approximately 150°, with 120° of hip flexion and 30° of hip extension. Comparing area 258 with area 250 from FIG. 12a shows that the total range of motion for assembly 220 is equivalent to able-bodied range of motion.

Area 260 shows a range of motion of system joint 30 during a running gait speed in which compliant actuation assembly 220 is able to supply a flexion torque $\tau_2$. Total range of motion through which assembly 220 can supply a flexion torque $\tau_2$ during a running gait speed is approximately 46°, beginning from −5° and flexing through neutral to 41°, centered at 18°.

Area 262 shows a range of motion of system joint 30 during a running gait speed in which compliant actuation assembly 220 is able to supply an extension torque $\tau_1$. Total range of motion through which assembly 220 can supply extension torque $\tau_1$ during a running gait speed is approximately 46°, beginning from 50° and extending to 4°, centered at 27°. Comparing area 260 and 262 with area 254 from FIG. 12a shows that the torque-supported running range of motion for assembly 220 covers the full able-bodied running range of motion (−5° to 50°).

Area 264 shows a range of motion of system joint 30 during stair climbing in which compliant actuation assembly 220 is able to supply an extension torque $\tau_1$. Total range of motion through which assembly 220 can supply extension torque $\tau_1$ during stair climbing is approximately 46°, beginning from 64° and extending to 18°, centered at 41°. Supplying extension torque $\tau_1$ during stair climbing helps to pull the body upwards, up the stairs. Comparing area 264 with area 256 from FIG. 12a shows that the range of torque-supported hip extension by assembly 220 is similar to able-bodied stair climbing range of motion.

Figure 13:
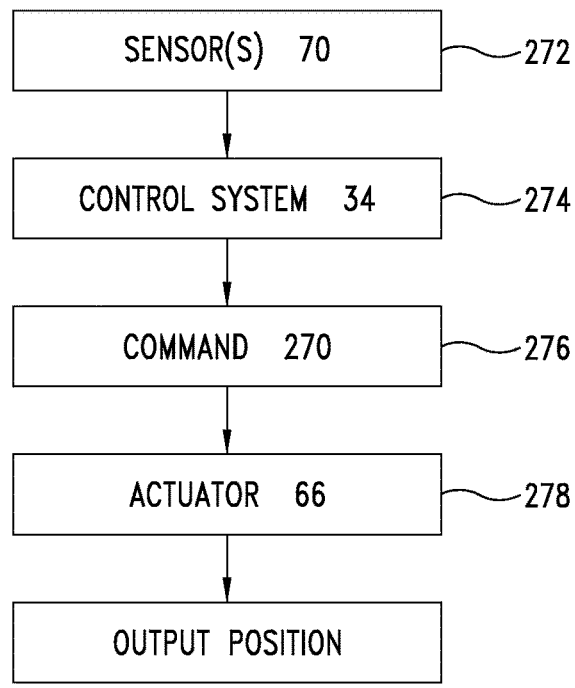
FIG. 13 illustrates a method of controlling a compliant joint actuation system.
Figure 19:
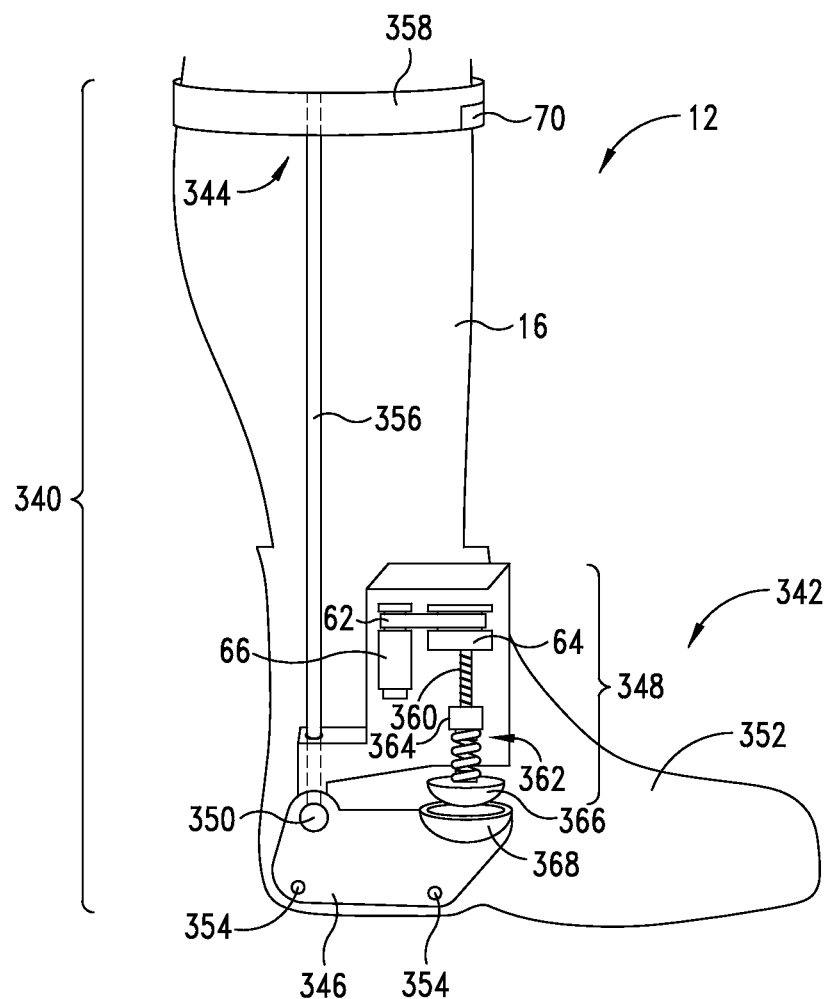
FIG. 19 illustrates a compliant joint actuation system worn at an ankle joint of a user.

FIG. 13 shows a block diagram of a method of controlling a compliant joint actuation system. Information from sensors 70 are inputs for control system 34. In one embodiment, control system 34 relates an input from sensor 70 and outputs a command 270 to actuator 66 in order to control a position of a nut, including nut 90 from assembly 20 (FIG. 4b), nut 136 from assembly 130 (FIG. 7), nut 166 from assembly 160 (FIG. 8), nut 236 from assembly 220 (FIG. 11a), or nut 364 from assembly 348 (FIG. 19). The method for controlling compliant joint actuation system 10 includes the steps of sensing or measuring 272 a physical characteristic of user 12 or system 10 using sensors 70, processing 274 with control system 34 the sensed physical characteristic, generating 276 a command 270 for actuator 66, controlling 278 a position of actuator 66 into an output position.

During the step of sensing 272, sensors 70 detect one or more physical characteristics or physical states of user 12 any compliant joint actuation system 10. One or more sensors 70 may be disposed on a limb or joint of user 12, such as a hip joint, ankle joint, lower leg, thigh, foot, or other part of user 12 to measure or detect a physical characteristic of a limb or joint of user 12. One or more sensors 70 may be disposed on a joint, linkage, or other component of compliant joint actuation system 10 to measure or detect a physical characteristic of the system. A sensor 70 may include an accelerometer, vibrometer, rate gyro, potentiometer, inclinometer, pressure transducer, force transducer, load cell, or other sensor or combination of sensors. In one embodiment, sensing 272 includes a continuous measurement with sensors 70.

During the step of processing 274 the signal from sensors 70, information about the user's position is determined, as well as information about a system joint, the motor, the nut, or the compliant elements. The step of processing 274 may include conditioning and transformation steps. Conditioning is realized by any filtering method including Kalman filtering, transfer function use, integration, pseudo integration, differentiation, pseudo differentiation, and amplification. Amplification may result from a gain of any nonzero number, including by a unity gain. Transformation may include a change in coordinate systems, change of scale, isometric or non-isometric transformation, rotation, dilation, projection, or other mathematical function.

In one embodiment, one of sensors 70 includes a motor encoder on actuator 66 to provide a closed-loop control. A position sensor is disposed on system joint 30 correlates to a position of the user's anatomical hip, and thus, the position measurement of a system joint provides information about a user's anatomical position. One or more position sensors 70 are used to measure deflection in one or more compliant elements. Motor position, the user's hip position, and spring deflection are used as inputs for the steps of processing 274 and generating 276 a command 270 to actuator 66. In one embodiment, the output position of actuator 66 controls a position of a nut. By controlling a position of the nut, the deflection in compliant elements is controlled.

Figure 14:
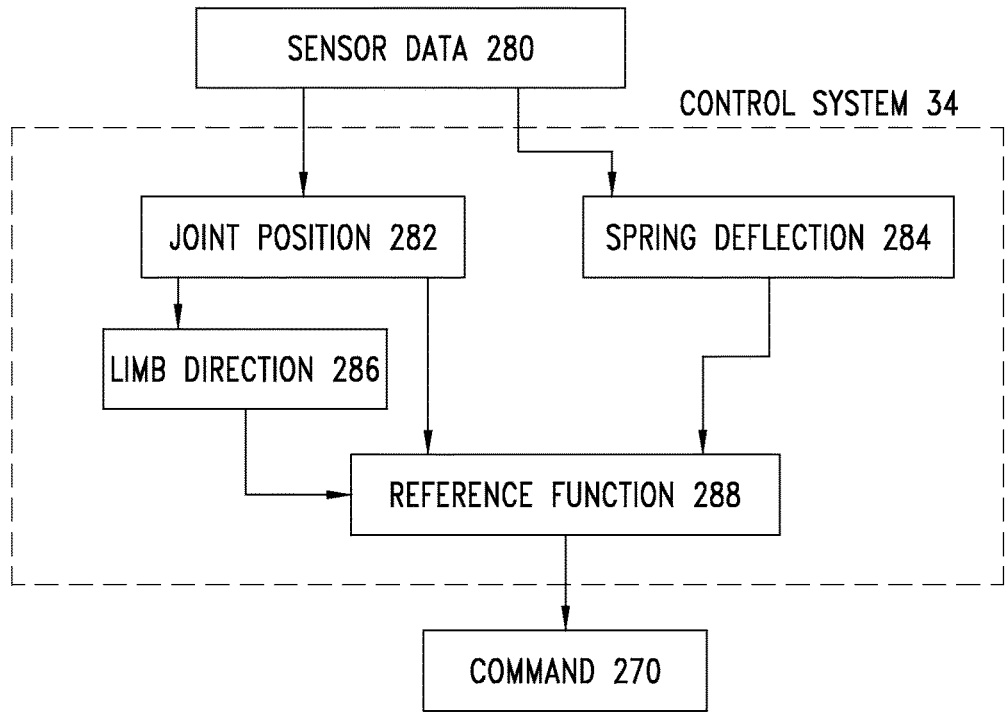
FIG. 14 illustrates additional detail of a method of controlling a compliant joint actuation system.

FIG. 14 shows additional detail of a method of controlling a compliant joint actuation system. The step of sensing 272 a characteristic from sensor 70 generates sensor measurements or data 280. Sensor data 280 may include angular position, linear position, linear velocity, angular velocity, linear acceleration, angular acceleration, moment, force, load, inertia or information. Data 280 from sensor 70 is processed using control system 34 to generate a command 270. In one embodiment, sensor data 280 undergoes processing steps, including optional conditioning and/or transformation steps, to determine a joint position 282 and spring deflection 284. Joint position 282 is further processed by control system 34 to determine a direction 286 of motion of the limb. Limb direction 286 is used an input into a reference function 288. Motor position, as well as joint position 282 and spring deflection 284, are also used inputs for reference function 288. Reference function 288 yields a command 270 based on a position of actuator 66, limb direction 286, joint position 282, and spring deflection 284. Command 270 controls the output position for actuator 66.

Figure 15:
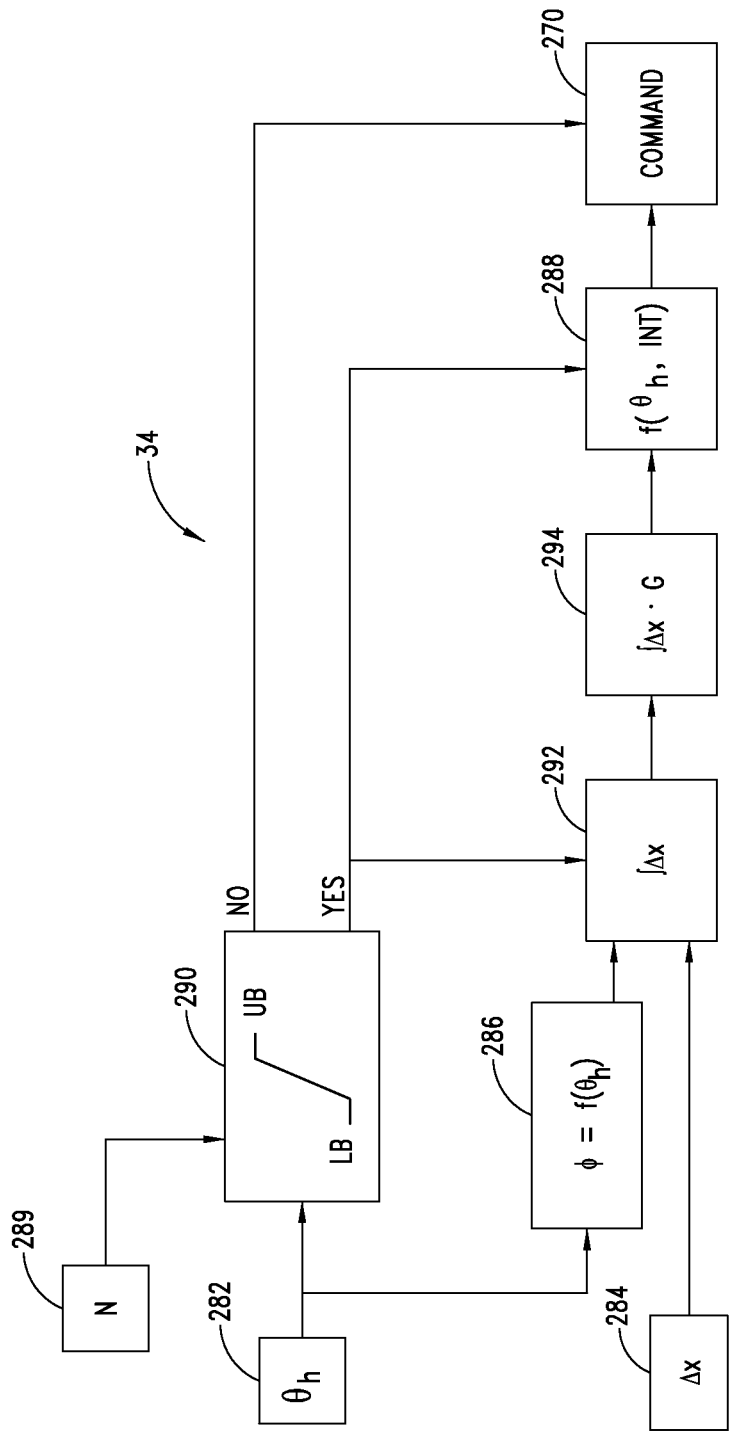
FIG. 15 illustrates a method of processing sensor data for controlling a compliant joint actuation system.

FIG. 15 shows a method of processing sensor data for controlling a compliant joint actuation system. For compliant joint actuation system 10, a joint position 282 used as an input to control system 34 includes angular hip position $\theta_h$. In one embodiment, angular hip position $\theta_h$ is measured using a position encoder disposed directly on system joint 30, and the angular position of system joint 30 correlates to the angular position of the user's anatomical hip joint. In another embodiment, angular hip position $\theta_h$ is determined indirectly by measuring a physical characteristic of a limb of user 12. For example, a rate gyro disposed on the user's leg gives an angular velocity of the limb. An angular velocity of the limb is integrated to obtain an angular position of the limb. Pseudo integration may be used to control drift of the angular position calculation.

An actuator position 289 used as an input to control system 34 includes nut position N. In one embodiment, nut position N is measured using a motor encoder disposed on actuator 66, where a position of actuator 66 correlates to nut position N.

Nut position N or angular hip position $\theta_h$ is input into a boundary condition function 290 to determine if nut position N or angular hip position $\theta_h$ falls within a set of boundaries, such as upper bound UB and lower bound LB. Where boundary conditions 290 are not met, a command 270 is generated to match angular hip position $\theta_h$. By matching angular hip position $\theta_h$, the nut position follows the hip path, and user 12 feels no resistance from the system 10. Where boundary conditions 290 are met, additional processing steps are used to generate command 270. For example, when nut position N or angular hip position $\theta_h$ moves beyond upper bound UB and lower bound LB, an integrator function 292 is employed in generating command 270.

Inputs of integrator function 292 include angular hip position $\theta_h$, spring deflection 284, as well as a phase angle $\phi$ of the hip. Phase angle $\phi$ is calculated from angular hip position $\theta_h$ and is used to determine limb direction 286. In one embodiment, phase angle $\phi$ of the hip is determined by a trigonometric function of angular hip position $\propto_h$ and angular hip velocity $\dot{\theta}_h$. In one embodiment, angular hip position $\theta_h$ is measured at the system joint 30, and angular hip velocity $\dot{\theta}_h$ is calculated by taking the time derivative of angular hip position $\theta_h$. In another embodiment, angular hip velocity $\dot{\theta}_h$ is measured using a rate gyro, and angular hip position $\theta_h$ is calculated by pseudo integrating angular hip velocity $\dot{\theta}_h$. Phase angle $\phi$ is represented generally as a function of angular position and angular velocity by equation (2).

$$\phi = f(\theta_h, \dot{\theta}_h) \quad (2)$$

Where $\phi$=phase angle of the hip
$\theta_h$=angular position of the hip
$\dot{\theta}_h$=angular velocity of the hip The trigonometric function used to determine phase angle may include sine, cosine, tangent, arcsine, arccosine, arctangent, or other function. In one embodiment, the phase angle $\phi$ is determined using a phase plane, with an x-coordinate based on angular hip position $\theta_h$ and a y-coordinate based on angular hip velocity $\dot{\theta}_h$. A phase plane is used to shift a phase angle $\phi$ to determine a limb direction 286 and is represented by equation (3).

$$\phi = (\theta_h - 90°, \dot{\theta}_h / 1000) \quad (3)$$

Where $\phi$=phase angle of the hip
$\dot{\theta}_h$=angular position of the hip
$\dot{\theta}_h$=angular velocity of the hip Equation (3) produces phase angle $\phi$ as a step function that simplifies the motion of the limb into a step function, creating a signal that varies between a positive and a negative value. A positive value indicates a first direction of motion, and a negative value indicates an opposite direction of motion. Limb direction 286 gives the relative motion of the user and is used as an input to integrator function 292 to determine a characteristic, such as a direction, of integrator function 292 used to integrate spring deflection 284.

Based on boundary condition 290 being met and limb direction 286 determining the behavior integrator function 292, spring deflection 284 is then input into integrator function 292. The integrated spring deflection is then filtered 294. In one embodiment, filtering 294 includes multiplying the integrated spring deflection by a gain, shown by equation (4).

$$INT = \int \Delta x \cdot G \quad (4)$$

Where $\Delta x$=spring deflection
G=gain

The result of equation (4) gives an integrated spring deflection filtered by a gain. The filtered integrated spring deflection is input into a reference function 288. Angular hip position $\theta_h$ is also an input into a reference function 288. An example of reference function 288 is shown by equation (5).

$$\text{Output position} = \theta_h + \int \Delta x \cdot G \quad (5)$$

Where $\theta_h$=angular position of the hip
$\Delta x$=spring deflection
G=gain Command 270 is an output of control system 34 and gives an output position for actuator 66 to position a nut. The output position is based on a set of calculations based on the user's hip position, motor position, and spring deflection. The system does not require any predefined nut path and instead is based on what the user is currently doing with the leg. Thus, control system 34 is user-based, i.e. controlled based on the user's real-time movements, thereby providing more accurate control of compliant joint actuation system. Because command 270 directly controls actuator position 289, and because actuator position 289 is an input to control system 34, the system operates as a feedback loop. As actuator position 289 adds spring deflection 284, and spring deflection 284 is input back into control system 34, more spring deflection is produced by the feedback loop.

Command 270 is based on angular hip position $\theta_h$, nut position N, and/or or spring deflection 284. If boundary conditions 290 are not met, command 270 will position the nut to match angular hip position $\theta_h$. If boundary conditions 290 are met, command 270 is based on both spring deflection 284 and angular hip position $\theta_h$. Command 270 will position nut to add deflection to the spring. Because spring deflection 284 is an input to reference function 288, a command 270 that adds spring deflection will cause the input spring deflection 284 to increase. With spring deflection 284 fed back into control system 34, adding spring deflection will in turn cause more spring deflection. Thus, integrator function 292 builds upon deflection in the spring to add more deflection. An example of a command path for nut 90 is shown in FIG. 16a.

Figure 16A:
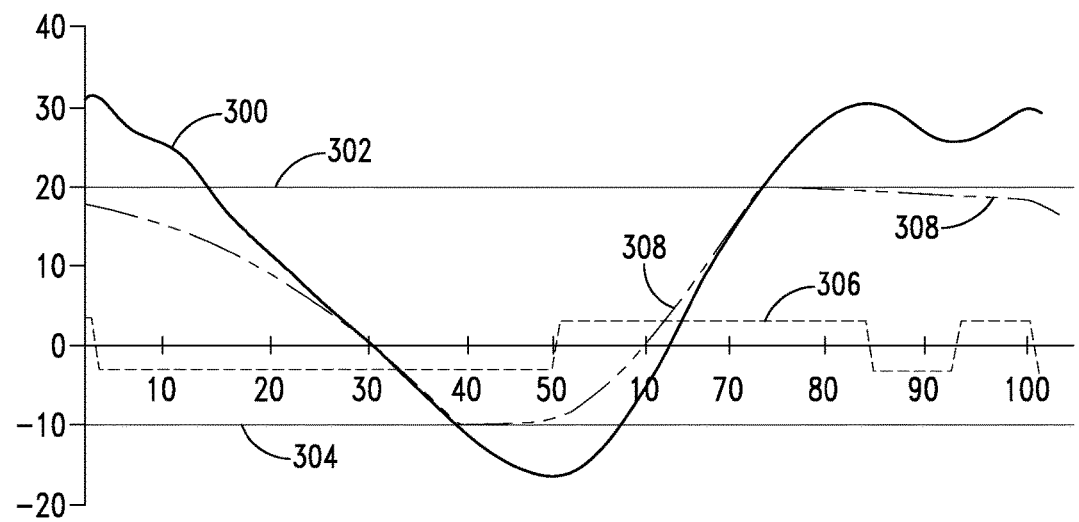
FIGS. 16a-16b illustrate a reference function and control path for a method of controlling a compliant joint actuation system.
Figure 16B:
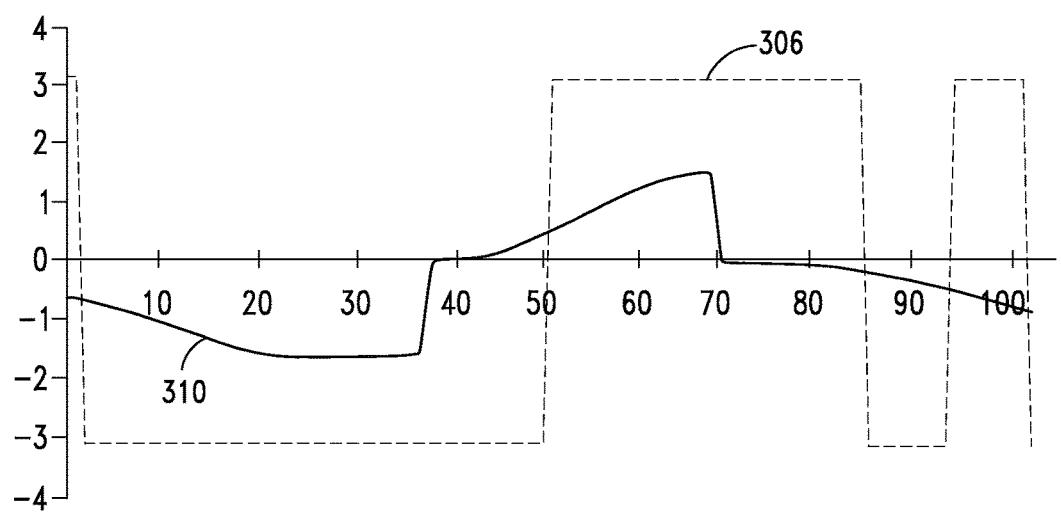

FIGS. 16a-16b show, in relation to FIGS. 13-15, a reference function and control path for a method of controlling a compliant joint actuation system. The x-axis of each graph shows a gait cycle in terms of percentage of a single gait cycle for one leg of user 12 beginning with a heel strike. In one embodiment, the first 60% of the gait cycle represents stance phase, while the remaining 60%-100% of the gait cycle represents swing phase. A position of the user's hip joint 100 relates to the position of the user's leg. Hip position is measured with respect to a neutral position, shown as 0 degrees on the y-axis in FIG. 16a. The user's leg changes direction at approximately 0% and 50% of the gait cycle.

In FIG. 16a, the y-axis of the graph shows position measured in degrees relative to a vertically neutral position of leg 16. Line 300 shows an example of angular hip position eh throughout a single gait cycle. A heel strike is represented at zero on the x-axis (0% of the gait cycle) and marks the beginning of stance phase and the beginning of a gait cycle. At heel strike, the user's leg 16 is flexed forward approximately 30°. From heel strike, the leg begins to extend backward to push the body over the foot. The negative slope of line 300 between 0%-50% of the gait cycle represents hip extension during stance. At approximately 30% of the gait cycle represents mid-stance, where the hip is in a vertically neutral position. At approximately 50% of the gait cycle, hip is at maximum extension, shown as approximately −15° and the user begins push-off. The foot lifts from the ground and the user flexes the hip to swing the leg forward. The positive slope of line 300 between 50%-100% of the gait cycle represents hip flexion during swing phase. Between 80%-100% of the gait cycle, the user's leg is flexed fully forward, and may oscillate between approximately 25°-30° until the foot makes a heel strike.

Line 302 shows an upper boundary and line 304 shows a lower boundary for boundary conditions 290. Where angular hip position 300 or a nut position N extends above upper boundary 302 or below lower boundary 304, a boundary condition 290 is met, and integrator function 292 is employed in determining a nut position. Line 306 shows a phase angle φ of the hip, which correlates to limb direction 286. Once integrator function 292 is employed by meeting boundary conditions 290, phase angle 306 is used as an input to integrator function 292. Integrator function 292 is used in a reference function 288 to produce a command 270, which is an actuator path or a nut position. A nut position is shown by line 308. When integrator function 292 is employed, a nut position 308 begins to deviate from hip position 300, thereby producing deflection in a spring. The area between angular hip position 300 and nut position 308 correlates to spring deflection.

FIG. 16b shows a method of using phase angle with an integrator function to control compliant joint actuation system 10. Phase angle φ is used to determine a direction of integrator function 292. For example, line 310 illustrates an output of an integration. Control system 35 looks at phase angle 306 when angular hip position 300 crosses a boundary 302 or 304. Where phase angle 306 is a negative value, integrator operates in a direction shown in the positive region on the graph. For example, at 40% of the gait cycle in FIG. 16a, angular hip position 300 crosses lower boundary 304. At 40% of the gait cycle in FIG. 16b, phase angle 306 is $-\pi$. When phase ankle 306 is $-\pi$, an output of integration 310 is in the positive region. Therefore, integrator function 292 positions a nut to begins to add deflection into a spring. Line 310 in FIG. 16b compared with lines 300 and 308 in FIG. 16a show that the integrator builds slowly adding more and more spring deflection until the nut 308 catches up to the hip position 300. As the nut position 308 catches up with hip position 300, spring deflection decreases until the nut position 308 matches hip position 300 and spring deflection is zero, shown between approximately 65%-75% of the gait cycle.

Figure 17:
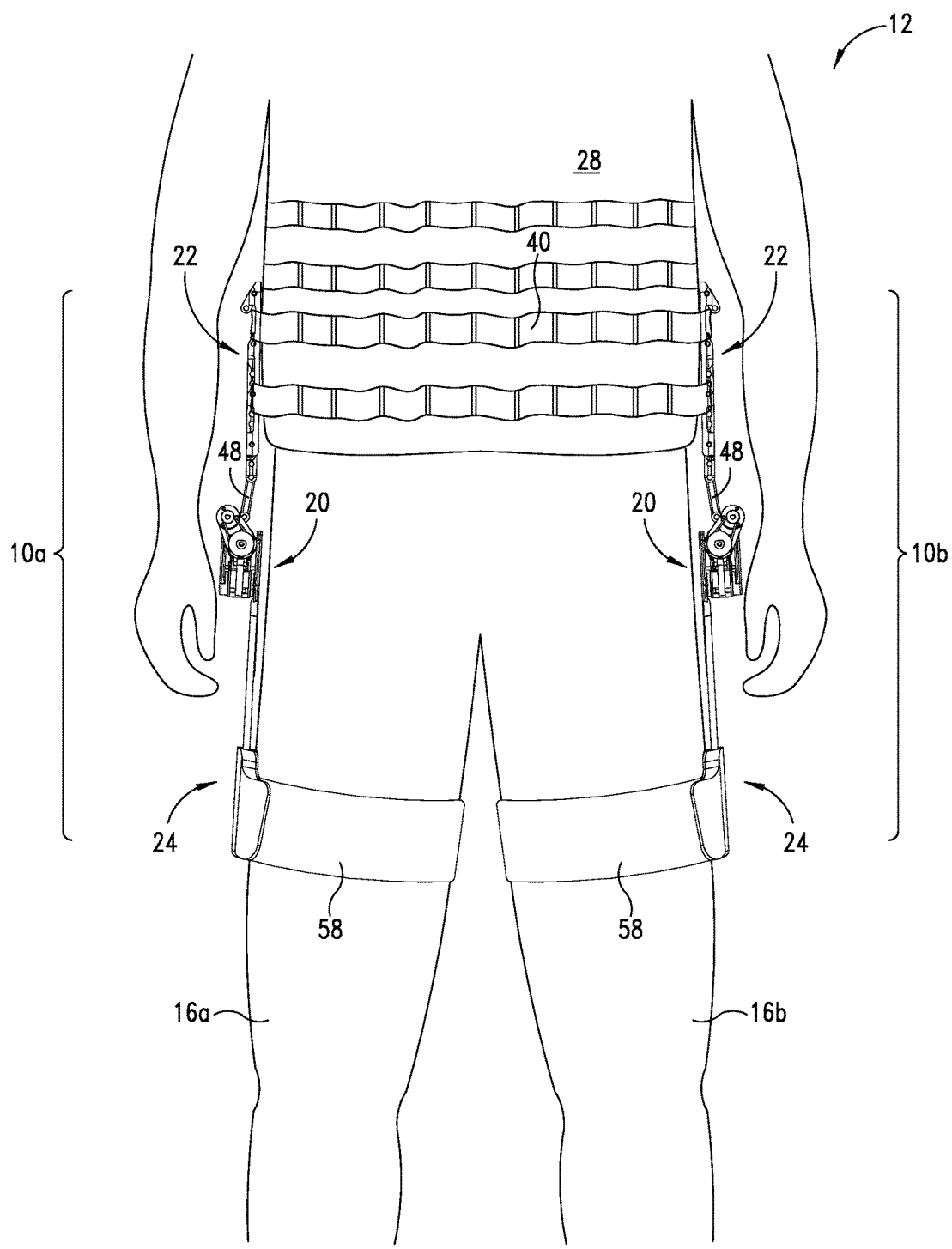
FIG. 17 illustrates a front view of a compliant joint actuation system worn at a hip joint of a user.

FIG. 17 illustrates a front view of a compliant joint actuation system worn at each hip joint of a user. A compliant joint actuation system 10 is worn on both the right and left hips and provide bi-directional torque assistance for each hip. Compliant joint actuation system 10 is compact and lightweight, which improves the efficiency of the system. The configuration of compliant actuation assembly 20 allows for a smaller power stroke, and thus, a smaller motor. In a screw drive actuation scheme, a smaller motor stroke also allows a shorter screw to be used, and reduces the size of the assembly. With a smaller motor and screw drive and more compact assembly, the position of the actuation assembly within the overall compliant joint actuation system 10, as well as the position on the user, is more versatile. For example, compliant joint actuation system 10 is positioned on user 12 with the screw-drive oriented in a horizontal position at the hip. The size and position of compliant actuation assembly 20 reduces interference of the components with the user's range of motion. Additionally, the weight of compliant joint actuation system 10 is lighter than existing exoskeletons for joint assistance.

Figure 18C:
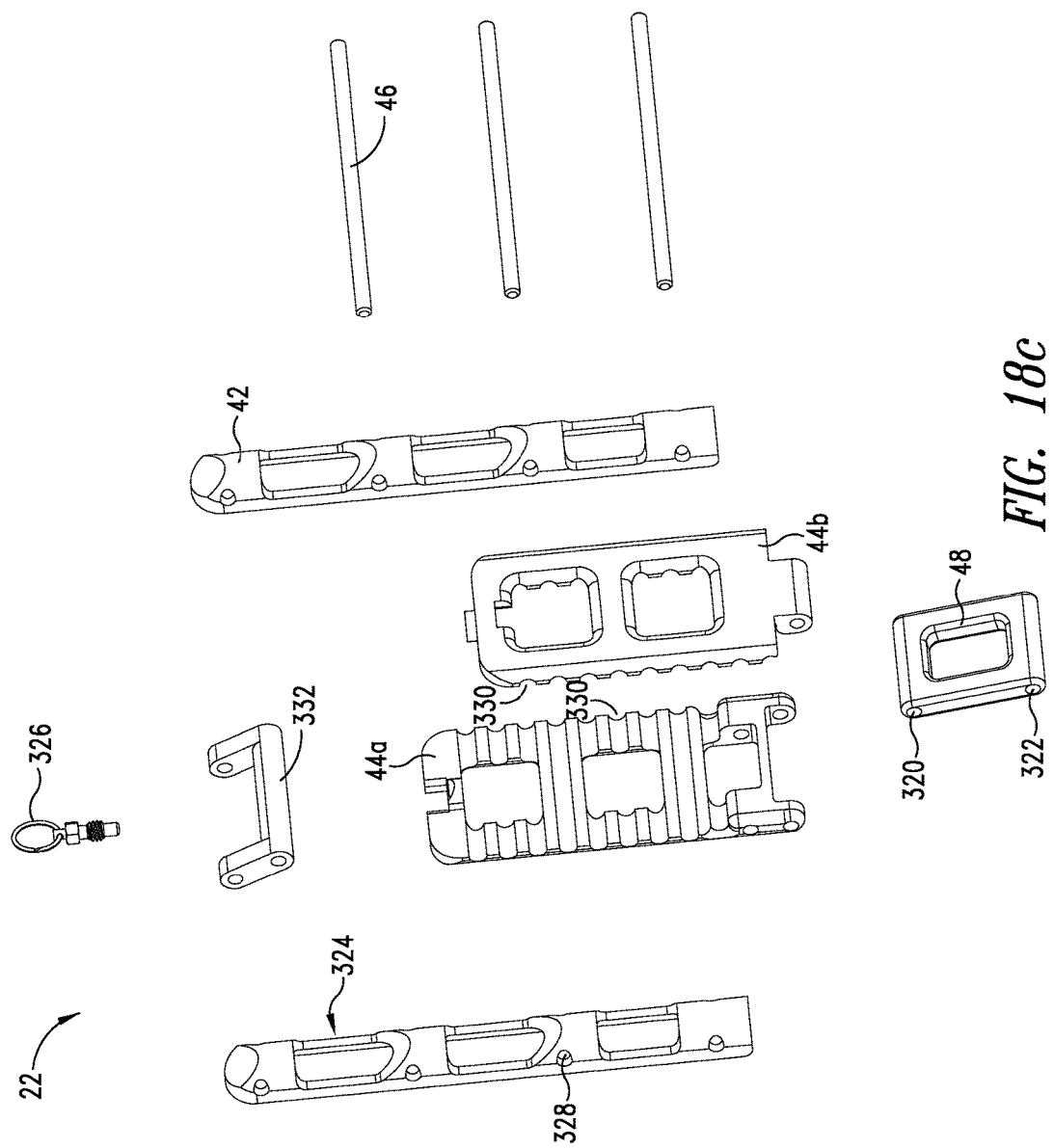

FIGS. 18a-18c show, in relation to FIGS. 1-2, a torso attachment assembly for a compliant joint actuation system. FIG. 18a shows a front view of torso attachment assembly 22 of compliant joint actuation system 10. Torso attachment assembly 22 couples to compliant actuation assembly 20 by a redundant link 48. Redundant link 48 couples to locking rack 44 by a joint 320 and to compliant actuation assembly 20 at joint 322. Redundant link 48 rotates in the coronal plane about joint 320 with respect to locking rack 44. Redundant link 48 rotates in the coronal plane about joint 322 with respect to compliant actuation assembly 20. Thus, redundant link 48 provides an extra degree of freedom in the coronal plane to permit abduction and adduction of leg 16 and allow compliant joint actuation system 10 to fit a variety of body types. A position of redundant link 48 on compliant actuation assembly 20 is adjustable and can be positioned in the sagittal plane for proper alignment of the system joint 30 on user 12.

FIG. 18b shows an isometric view of torso attachment assembly 22 of compliant joint actuation system 10. Stakes 42, pins 46, and locking rack 44 fit together among webbing of an IOTV vest 28 to rigidly affix compliant joint actuation system 10 to the user's torso to resist torque in the sagittal plane. Webbing 40 fits over stakes 42 and within grooves 324 of stakes 42. A position of stakes 42 and locking rack 44 is selected to align system joint 30 with anatomical hip joint 100 of user 12. Stakes 42 include a plurality of openings 328 into which pins 46 are inserted. Locking rack 44 can be moved vertically between stakes 42 for vertical adjustment of lacking rack 44 with respect to stakes 42 and vest 28. A quick release 326 holds locking rack 44 together. Locking rack 44 also includes a plurality of openings 330 into which pins 46 are inserted. Openings 330 are spaced closely together to allow fine vertical adjustment of locking rack 44 with respect to stakes 42. Webbing 40 of vest 28 under locking rack 44 and over stakes 42 with pins 46 holding locking rack 44 in place. A spacer link 332 is disposed between stakes 42 at an end of stakes 42 opposite to locking rack 44 to further resist rotation in the sagittal plane. A pin 46 holds spacer link 332 between stakes 42. Therefore, torso attachment assembly 22 includes a combination of rigid links that transmit a force or torque from compliant joint actuation system 10 to user 12. Torso attachment assembly 22 ensures torque produced by compliant joint actuation system 10 is efficiently transferred to the user's hip joint.

FIG. 18b shows an expanded view of torso attachment assembly 22 of compliant joint actuation system 10. Locking rack 44 comprises two portions 44a-44b which fit around pins 46. Pins 46 hold locking rack 44 in place, while stakes 42 hold pins 46 and locking rack 44 to vest 28. In one embodiment, locking rack 44 comprises two portions 44a-44b held together by a quick release 326 to allow easy donning and doffing of compliant joint actuation system 10.

FIG. 19 shows a compliant joint actuation system worn at an ankle joint of a user. Compliant joint actuation system 340 operates as a wearable device for assisting user 12 with the movements associated with human gait. User 12 wears a compliant joint actuation system 340 in order to add assistive energy to the user's step and reduce the metabolic cost of gait. In one embodiment, a compliant joint actuation system 340 is worn on each foot 342 in proximity to the user's anatomical ankle joint in order to add a force or torque to the ankle joint. Each compliant joint actuation system 340 provides uni-directional force or torque to the user's ankle joint. Adding force or torque at specific timing during the user's gait reduces metabolic energy required from user 12 to produce a gait step. Compliant joint actuation system 340 applies a force or torque near ankle joint during the push off phase of each gait step for each leg 16. Applying torque at an ankle joint during push off assists user 12 with plantarflexion. For greater joint torque assistance, two compliant joint actuation systems 340 are worn on each ankle, with a compliant actuation assembly 348 worn on each side of each foot 342. Therefore, user 12 wears one or more compliant joint actuation systems 340 to assist with gait.

Compliant joint actuation system 340 includes a leg attachment 344, a footwear attachment 346, and a compliant actuation assembly 348. Compliant joint actuation system 340 is secured to user 12 at two attachment points on user 12, foot 342 and lower leg 16, with the user's ankle joint located in between the two attachment points. Leg attachment 344 and a footwear attachment 346 provide for wearability of the system and transfer the forces from compliant actuation assembly 348 to the limbs and joints of user 12. Compliant actuation assembly 348 includes an effective ankle joint 350, which operates as the system joint. Compliant actuation assembly 348 applies a torque at effective ankle joint 350. Compliant actuation assembly 348 is disposed in proximity to the user's anatomical ankle joint to position an effective ankle joint 350 of compliant joint actuation system 340 in proximity to the user's ankle joint. System joint 350 comprises a spherical joint that permits a full range of motion of the user's ankle joint.

Footwear attachment 346 is configured to couple to a user's footwear 352 by one or more joints 354, or is incorporated into footwear 352. In one embodiment, footwear attachment 346 includes a heel bracket rigidly affixed to footwear 352. Leg attachment 344 is configured to couple to a user's leg 16. Leg attachment 344 includes a lever 356 and strap, sling, or cuff 358. In one embodiment, user 12 wears cuff 358 on lower leg 16. Lever 356 extends from cuff 358 to footwear attachment 346 and couples to effective ankle joint 350. Lever 356 operates to transfer the torques generated by compliant actuation assembly 348 to user's leg 16. Lever 356 includes a lightweight rigid material and may include a metal, metal alloy, polymer, fiberglass, carbon fiber, composite material, natural material, or other suitable material. In one embodiment, lever 356 includes carbon fiber tubing. Leg attachment 344 and footwear attachment 346 are configured to allow mobility and a natural range or motion for user 12 without encumbering or restricting the user's gait.

Compliant actuation assembly 348 includes an active compliant mechanism having one or more active elements and one or more compliant elements. Active elements may include motors or actuators. Compliant elements may include helical, coil, or torsional springs, leaf springs, bumpers, cables having elastic properties, or other types of compliant device. In one embodiment, compliant actuation assembly 348 is powered by an active member, such as a motor-driven screw 360, and a compliant member, such as a coil spring 362, arranged in series. In another embodiment, an active element of compliant actuation assembly 348 is powered by a controllable position actuator or a force-type actuator, and may include a hydraulic, pneumatic, rotary, direct-drive, series-elastic, electroactive polymer-based, chemical-based, or other actuation scheme.

A motor-driven screw 360 is driven by a belt drive assembly or belt 62 coupled by a bracket 64 to an actuator 66. Actuator 66 couples to screw 360 to rotate or drive screw 360 and produce rotary motion. Screw 360 includes one or more bearings, such as radial bearings and thrust bearings, at a proximal end of screw 360. Actuator 66 couples to the proximal end of screw 360 to drive screw 360 in either the clockwise direction or counter-clockwise direction based on a command or motor control pattern received by actuator 66 from control system 34. Actuator 66 is a position-type actuator that positions a nut 364, such as a lead screw, along screw 360. Nut 364 is threaded onto screw 360 and which translates linearly along screw 360 as screw 360 is rotated by actuator 66. Nut 364 couples spring 362 to screw 360. Spring 362 terminates at a bumper 366, which interfaces with a spring receptacle or spring cup 368. Bumper 366 and spring cup 368 form a spherical joint that permits a full range of motion of the user's ankle joint. Bumper 366 is configured to engage and disengage from spring cup 368. Actuator 66 moves nut 364 to position bumper 366. Once bumper 366 contacts spring cup 368, spring 362 is engaged. Deflection is added to spring 362 by the movement of user 12 and by a position of nut 364 as controlled by actuator 66. As leg 16 rolls over foot 342, the position of the leg 16 adds compression in spring 362. Actuator 66 moves nut 364 toward spring 362 to add more compression in spring 362. At push off, the energy stored in spring 362 is returned to the user. Spring 362 applies a force through bumper 366 directed into spring cup 368, which produces a torque at system joint 350.

Compliant actuation assembly 348 couples to a control system, such as control system 34 from FIG. 1, wirelessly or by wired connection. Compliant joint actuation system 340 is controlled using an input from one or more sensors 70. Sensors 70 may include one or more sensors disposed on compliant joint actuation system 340 or worn by user 12. Sensors 70 detect a physical characteristic or physical state of a mobile body, such as a limb of user 12 or a link of compliant joint actuation system 10. A sensor 70 may be disposed on a limb or joint of user 12, such as a hip joint, ankle joint, lower leg, thigh, foot, or other part of user 12 to measure or detect a physical characteristic of a limb or joint of user 12. Sensors 70 may be disposed on a joint, linkage, or other component of compliant joint actuation system 340 to measure or detect a physical characteristic of the system. Sensors 70 may be disposed on the system to indirectly measure a physical characteristic of user 12. For example, a position sensor disposed on effective ankle joint 350 correlates to a position of the user's anatomical ankle, and thus, the position measurement of a system joint provides information about a user's anatomical position.

A sensor 70 may include an accelerometer, vibrometer, rate gyro, potentiometer, inclinometer, pressure transducer, force transducer, load cell, or other sensor or combination of sensors. The physical characteristic or physical state measured by sensors 70 include a kinematic state, a loading state, or a kinematic state and a loading state. A kinematic state includes an angular position, linear position, linear velocity, angular velocity, linear acceleration, or angular acceleration associated with a mobile body with reference to a fixed global frame or a frame fixed to any other mobile body. A loading state includes a moment or force experienced by the mobile body. In one embodiment, sensors 70 continuously measure information about the system or about the user.

Information from sensors 70 is used as inputs for control system 34, which produces an output command to actuator 66. In one embodiment, the output command is a position for actuator 66. The position of actuator 66 determines a force that is applied to footwear attachment 346 by compliant actuation assembly 348.

Figure 20A:
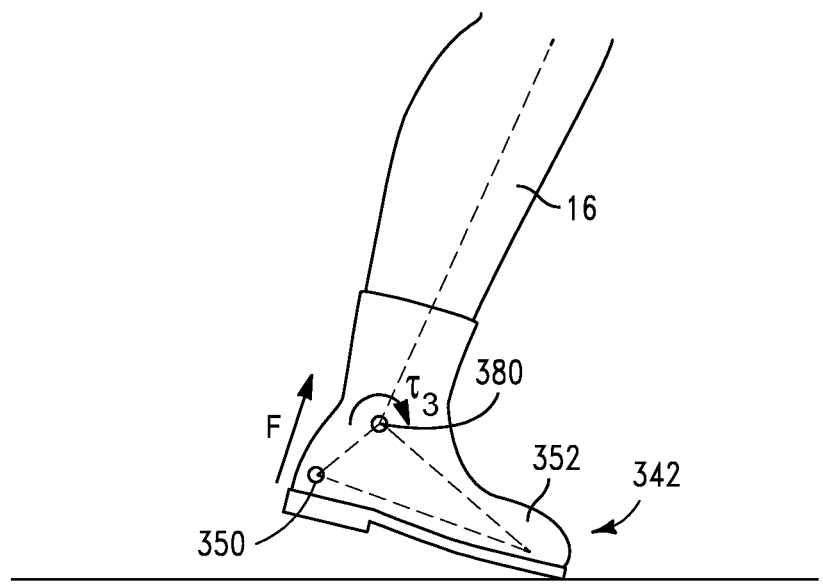
FIGS. 20a-20d illustrate a method of using a compliant joint actuation system for an ankle joint.

FIGS. 20a-20d show a method of using a compliant joint actuation system for an ankle joint. FIG. 20a shows a schematic representation of a compliant joint actuation system 340 for an ankle joint 380. In FIG. 20a, compliant joint actuation system 340 is positioned on user 12 to apply a torque or force F to footwear 352, which produces a torque $\tau_3$ about ankle joint 380.

Figure 20B:
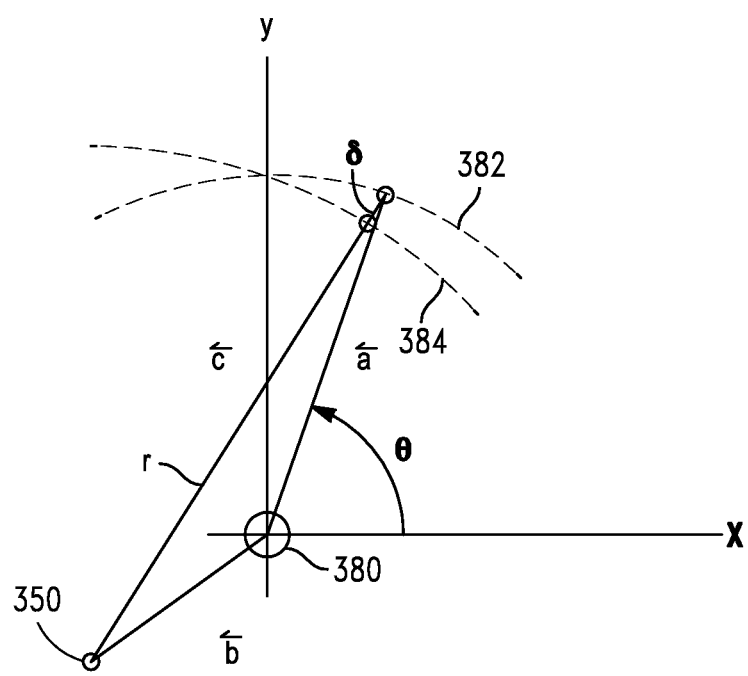

FIG. 20b shows a schematic of compliant joint actuation system 340 for an ankle joint. Compliant joint actuation system 340 includes a system joint 350, which operates an effective ankle joint of compliant joint actuation system 340. System joint 350 is not required to align with ankle joint 380 in order to produce an assistive torque at the user's ankle joint 380. Rather, compliant joint actuation system 340 accounts for misalignment of system joint 350 and ankle joint 380. In one embodiment, system joint 350 and ankle joint 380 are intentionally misaligned. By intentionally misaligning the joints, the order of magnitude and general direction of the misalignment are more easily defined. The additional rotation and translations to accommodate the misalignment are accounted for in the attachment of compliant joint actuation system 340 to a lower leg 16 and foot 342. Lines 382 and 384 show a translational error δ as lower leg 16 rotates. Where system joint 350 is disposed low and behind ankle joint 380, translational error δ grows in magnitude as vector ⌣, representing lower leg 16, rotates towards the x-axis. Length r represents the rotational driving link of compliant joint actuation system 340. Vector ⌣ represents the mathematical distance between system joint 350 and cuff 358. Vector ⌣ represents the fixed offset or misalignment system joint 350 from ankle joint 380. Vector ⌣, vector ⌣, and length r are defined, thus vector ⌣ and translational error δ is determined using equations (6) and (7).

$$\overset{\frown}{} = \overset{\frown}{} + \overset{\frown}{} \quad (6)$$

$$\delta = r - |c| \quad (7)$$

If the magnitude of vector ⌣ is much greater than the magnitude of vector ⌣, then the magnitude of translational error δ is much less than length r. Because the tolerances of human joints can be determined, the magnitude of misalignment of system joint 350 and ankle joint 380 is predictable such that the gear ratios of compliant joint actuation system 340 are adjusted to compensate for the misalignment.

Figure 20C:
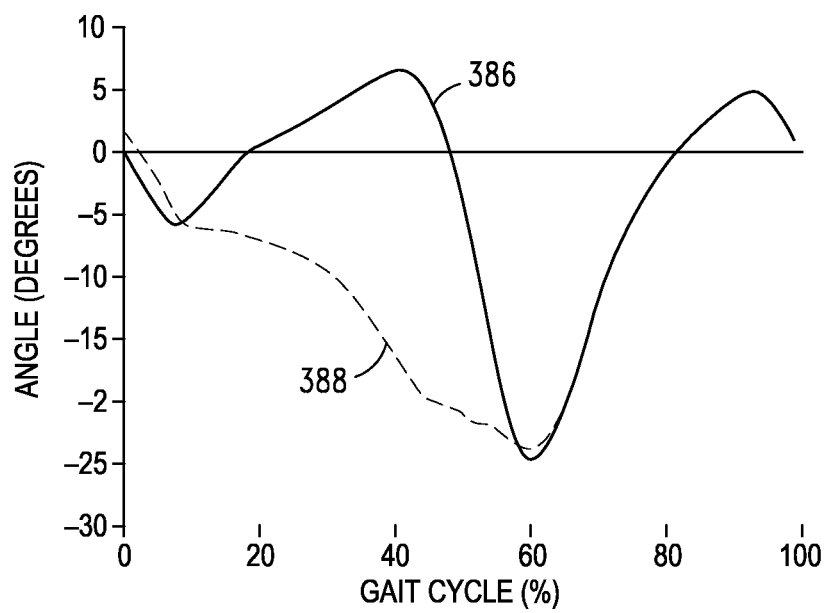

FIG. 20c shows the path of actuator 66 for compliant joint actuation system 340. Line 386 represents ankle position for able-bodied gait. Heel strike occurs at 0% of the gait cycle. After heel strike, foot 342 begins to rotate in the direction of plantarflexion, indicated by the negative slope of line 386 between 0%-10% of the gait cycle. After foot 342 is flat on the ground, leg 16 begins to roll over the foot. The positive slope of line 386 between 10-40% indicates the dorsiflexion direction of foot 342 with respect to leg 16. Push-off occurs at approximately 50% of the gait cycle, with the negative slope of line 386 showing plantarflexion of foot 342. Compliant joint actuation system 340 applies a force or torque near ankle joint of user 12 during the push off phase of each gait step for each leg 16.

Line 388 represents a path for actuator 66 to assist with push off. At 10%, actuator 66 moves nut 364 to allow bumper 366 to engage with spring cup 368. Once bumper 366 contacts spring cup 368, deflection is added to spring 362 by the movement of user 12 and by a position of nut 364 as controlled by actuator 66. As leg 16 rolls over foot 342, the position of the leg 16 adds compression in spring 362. The area between lines 386 and 388 represents the deflection in spring 362. The stiffness of spring 362 is selected to optimize the motor path, line 388, to achieve a minimum peak power required from actuator 66. Actuator 66 moves nut 364 toward spring 362 to add more compression in spring 362. At push off, the energy stored in spring 362 is returned to the user. Spring 362 applies a force through bumper 366 directed into spring cup 368, which produces a torque at system joint 350. In one embodiment, actuator 66 continues to move toward spring 362 throughout push-off in order to add torque to the ankle joint throughout push-off.

The method for controlling joint system 340 using control system 34 includes the step of sensing 272 a physical characteristic of user 12 or joint system 340. The step of sensing 272 may further include sensing information about the state or position of actuator 66, nut 364, or spring 362. The method for controlling joint system 340 using control system 34 includes the steps of processing 274 the information from the sensor or sensors 70 using control system 34, and generating 276 a command 270 for actuator 66. During the step of sensing 272, sensors 70 continuously measure a user's ankle position, deflection in spring 362, and a state of actuator 66. In one embodiment, sensors 70 detect a kinematic state, a loading state, or a kinematic state and a loading state. Additional sensors may be used to continuously measure a state of actuator 66, spring 362, or other component of joint system 340 or control system 34. For example, sensor 70 may detect a force on spring 362 or position of actuator 66, to determine a moment on the user's joint.

During the step of processing 274 the signals from sensors 70, control system 34 determines information about the user's position or gait. In one embodiment, the continuous measurements from sensors 70 are filtered and conditioned to obtain the user's speed, stride length, or percent of gait cycle. Other gait information may include current joint torque, joint angle, limb position, and magnitude of force or moment at a joint. The gait information is further processed to obtain a command 270 for actuator 66.

During the step of generating 276 a command 270, the processed measurements are input into a reference function. In one embodiment, the reference function for joint system 340 is derived from pre-recorded able-bodied data. In another embodiment, the reference function for joint system 340 is an integrator function similar to reference function 288 from FIG. 15. A command 270 is produced to drive actuator 66 in the proper direction in order to compress spring 362 to add torque at the ankle joint to assist user 12 with one or more gait activities. Such activities include walking, running, traversing slopes or stairs, avoiding obstacles, and other similar activities. Command 270 includes a command path, which is a position of actuator 36, such as a linear ramp, continuous drive, simple pulses, non-linear path, or other positional path. In contrast to if-then logic controllers, control system 34 uses continuous measurements to continuously determine the user's movement and determine an actuator 66 position to match the user's expected upcoming movement. In one embodiment, the processed measurement is compared with a recording or a calculation of able-bodied gait to determine or predict a desired gait activity. Command 270 is an output of control system 34 used to control actuator 66. Command 270 controls a position of actuator 66 which positions nut 364 and spring 362.

Figure 20D:
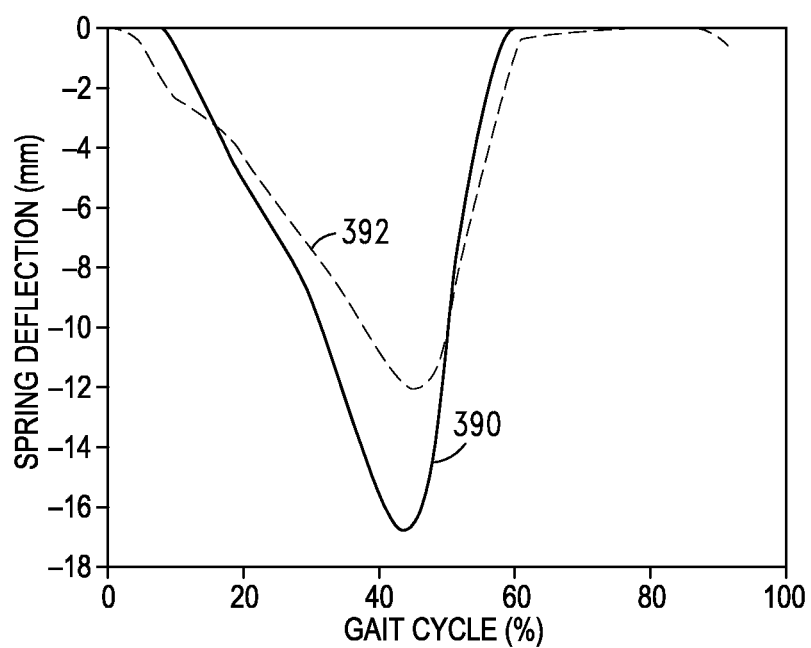

FIG. 20d is a graph of deflection in spring 362. Line 390 and line 392 each represent an example of spring deflection during a gait cycle. Heel strike occurs at 0% of the gait cycle. After heel strike, foot 342 begins to rotate in the direction of plantarflexion. Spring 362 is disengaged and at free length. In one embodiment, actuator 66 drives nut 364 upwards away from spring cup 368 to ensure spring 362 is disengaged. During stance phase, spring 362 re-engages. Actuator 66 positions nut 364 to engage spring 362 and to add deflection into spring 362. As leg 16 rolls over foot 342 during stance, the position of the leg 16 adds compression in spring 362. Spring deflection is maximized during push-off, at approximately 40%-50% of the gait cycle. At push off, the energy in spring 362 is released as spring returns to free length. Actuator 66 again disengages spring 362 during swing phase.

While one or more embodiments of the present invention have been illustrated in detail, the skilled artisan will appreciate that modifications and adaptations to those embodiments may be made without departing from the scope of the present invention as set forth in the following claims.

What is claimed:

1. A method of adding torque to a joint of a user, comprising:
   providing an actuation system including an actuator and a first and second spring;
   coupling a lever to a leg of the user and to the actuation system;
   measuring a position of the joint using a first sensor; and
   positioning the actuator to compress the first or second spring based on the position of the joint.

2. The method of claim 1, further including providing a control system to control the actuator based on the position of the joint.

3. The method of claim 1, further including:
   measuring a deflection in the first or second spring using a second sensor;
   integrating the deflection measurement using an integration function; and
   positioning the actuator based on the deflection measurement.

4. The method of claim 3, further including:
   determining a phase angle of the leg; and
   selecting the integration function based on the phase angle of the leg.

5. The method of claim 1, further including:
   adding torque to the joint in a first direction by compressing a first spring; and
   adding torque to the joint in a second direction by compressing a second spring.

6. The method of claim 5, further including:
   rotating the lever at a system joint of the actuation system; and
   aligning the system joint with the joint of the user.

7. A method of adding torque to a joint of a user, comprising:
   coupling a lever to a leg of the user;
   providing an actuator including a spring with the actuator coupled to the lever;
   measuring a position of the joint using a first sensor;
   measuring a deflection in the spring using a second sensor;
   integrating the deflection measurement using an integration function; and
   positioning the actuator based on the deflection measurement to deflect the spring.

8. The method of claim 7, further including coupling a control system to the actuator and the first sensor.

9. The method of claim 7, further including:
   determining a phase angle of the leg; and
   selecting the integration function based on the phase angle of the leg.

10. A method of adding torque to a joint of a user, comprising:
    coupling a lever to a leg of the user;
    providing an actuator including a spring with the actuator coupled to the lever;
    measuring a position of the joint using a first sensor;
    positioning the actuator to deflect the spring based on the position of the joint; and
    disengaging the spring during a non-gait activity.

11. The method of claim 10, further including disengaging the lever from the actuator during the non-gait activity.

12. The method of claim 10, further including:
    adding torque to the joint in a first direction by deflecting the spring in a first direction; and
    adding torque to the joint in a second direction by deflecting the spring in a second direction.

13. A joint actuation device, comprising:
    an actuation system including an actuator and a spring;
    a lever coupled to the actuation system and configured to couple to a leg of a user, the lever configured to rotate at a device joint with respect to the actuation system;
    a first sensor configured to measure a physical characteristic of the leg; and
    a control system configured to control the actuator based on the physical characteristic of the leg, wherein the actuator is configured to apply a torque to the device joint.

14. The joint actuation device of claim 13, wherein actuation system is configured to couple to a torso of the user, and the actuation system spans a hip joint of the user.

15. The joint actuation device of claim 14, wherein the torque at the device joint is aligned with the hip joint of the user.

16. The joint actuation device of claim 13, wherein actuation system is configured to couple to a foot of the user, and the actuation system spans an ankle joint of the user.

17. The joint actuation device of claim 16, wherein the torque at the device joint is positioned in proximity to the ankle joint of the user.

18. A joint actuation device, comprising:
    an actuation system including an actuator and a spring; and
    a lever coupled to the actuation system and configured to couple to a leg of a user, the lever configured to rotate at a device joint with respect to the actuation system, wherein the lever is configured to disengage from the actuation system during a non-gait activity.

19. The joint actuation device of claim 18, wherein actuator is to disengage the spring during the non-gait activity.

20. The joint actuation device of claim 18, further including:
    a sensor configured to measure a position of the device joint; and
    a control system coupled to the sensor and actuator, wherein the control system is configured to produce a command to control the actuator based on the position of the device joint.

21. The joint actuation device of claim 18, wherein actuation system is configured to couple to a torso of the user, and the actuation system spans a hip joint of the user.

22. The joint actuation device of claim 18, wherein actuation system is configured to couple to a foot of the user, and the actuation system spans an ankle joint of the user.

* * * * *